United States Patent [19]
Grossman et al.

[11] Patent Number: 5,807,682
[45] Date of Patent: *Sep. 15, 1998

[54] PROBE COMPOSITION CONTAINING A BINDING DOMAIN AND POLYMER CHAIN AND METHOD OF USE

[75] Inventors: Paul David Grossman, Burlingame; Steven Fung, Palo Alto; Steven Michael Menchen, Fremont; Sam Lee Woo, Redwood City; Emily Susan Winn-Deen, Foster City, all of Calif.

[73] Assignee: The Perkin-Elmer Corporation, Foster City, Calif.

[ * ] Notice: The term of this patent shall not extend beyond the expiration date of Pat. No. 5,470,705.

[21] Appl. No.: 877,460

[22] Filed: Jun. 17, 1997

Related U.S. Application Data

[63] Continuation of Ser. No. 561,478, Nov. 21, 1995, Pat. No. 5,703,222, which is a continuation of Ser. No. 866,018, Apr. 7, 1992, Pat. No. 5,470,705, which is a continuation-in-part of Ser. No. 862,642, Apr. 3, 1992, abandoned.

[51] Int. Cl.⁶ .............................. C12Q 1/68; C12P 19/34
[52] U.S. Cl. .............................. 435/6; 435/91.2; 436/94; 204/450; 204/451
[58] Field of Search .............. 435/6, 91.2; 204/450, 204/451; 436/94

[56] References Cited

U.S. PATENT DOCUMENTS

| | | | |
|---|---|---|---|
| 4,683,202 | 7/1987 | Mullis | 435/91.2 |
| 4,879,214 | 11/1989 | Kornher et al. | . |
| 4,883,750 | 11/1989 | Whiteley et al. | . |
| 4,925,785 | 5/1990 | Wang et al. | 435/6 |
| 5,011,769 | 4/1991 | Duck et al. | . |
| 5,061,361 | 10/1991 | Gordon | 204/299 R |
| 5,093,232 | 3/1992 | Urdea et al. | . |
| 5,108,568 | 4/1992 | Van Alstine | 204/180.1 |
| 5,171,534 | 12/1992 | Smith et al. | . |
| 5,470,705 | 11/1995 | Grossman et al. | . |
| 5,514,543 | 5/1996 | Grossman et al. | . |
| 5,580,732 | 12/1996 | Grossman et al. | . |

FOREIGN PATENT DOCUMENTS

WO92/08728  5/1992  WIPO .

OTHER PUBLICATIONS

Wu et al., Genomics 4, 560–569 (1989).
Cohen et al., Proc. Natl. Acad. Sci. USA 85, 9660–9663 (1988).
Noolandi, Electrophoresis 13, 394–395 (Jun. 1992).
Righetti, J. Chromatog. 516, 3–22 (1990).
Jorgenson et al., Science 222, 266–272 (1983).
Muller et al., Nucleic Acids Res. 9(1), 95–119 (1981).
Agrawal, S., and Tang, J.–Y., "Site–Specific Functionalization of Oligodeoxynucleotides for Non–Radioactive Labelling," *Tetrahedron Lett.* 31(11):1543–1546 (1990).

(List continued on next page.)

*Primary Examiner*—Kenneth R. Horlick
*Attorney, Agent, or Firm*—Peter J. Dehlinger; Vincent M. Powers

[57] ABSTRACT

Method and composition for detecting one or more selected polynucleotide regions in a target polynucleotide. In the method, a mixture of sequence-specific probes are reacted with the target polynucleotide under hybridization conditions, and the hybridized probes are treated to selectively modify those probes which are bound to the target polynucleotide in a base-specific manner. The resulting labeled probes include a polymer chain which imparts to each different-sequence probe, a distinctive ratio of charge/translational frictional drag, and a detectable label. The labeled probes are fractionated by electrophoresis in a non-sieving matrix, and the presence of one or more selected sequences in the target polynucleotide are detected according to the observed electrophoretic migration rates of the labeled probes in a non-sieving medium.

17 Claims, 15 Drawing Sheets

OTHER PUBLICATIONS

Barany, F., "Genetic Disease Detection and DNA Amplification Using Cloned Thermostable Ligase," *PNAS USA* 88:189–193 (1991).

Chen, et al., "Low–Cost, High–Sensitivity Laser–Induced Fluorescence Detection for DNA Sequencing by Capillary Gel Electrophoresis," *J. Chromatography* 559:237–246 (1991).

Cload, S.T., and Schepartz, A., "Polyether Tethered Oligonucleotide Probes," *J. Am. Chem. Soc.* 113:6324 (1991).

Cohen, A.S., et al., "High–Performance Capillary Electrophoretic Separation of Bases, Nucleosides, and Oligonucleotides: Retention Manipulation via Micellar Solutions and Metal Additives," *Anal. Chem.* 59(7):1021–1027 (1987).

Connell, C., et al., "Automated DNA Sequence Analysis," *BioTechniques* 5(4):342–348 (1987).

Cunico, R.L., et al., "Characterization of Polyethylene Glycol Modified Proteins Using Charge Reversed Capillary Electrophoresis," *J. Chromatog.* 559:467–477 (1991).

Duck, P., et al., "Probe Amplifier System Based on Chimeric Cycling Oligonucleotides," *BioTechniques* 9(2):152–147 (1990).

Haralambidis, J., et al., "The Synthesis of Polyamide–Oligonucleotide Conjugate Molecules," *Nuc. Acids Res.* 18(3):493–499 (1990).

Kambara et al., "Real Time Automated Simultaneous Double–Stranded DNA Sequencing Using Two–Color Fluorophore Labeling," *BioTechnology* 9:648–651 (1991).

Karger, et al., "Multiwavelength Fluorescence Detection for DNA Sequencing Using Capillary Electrophoresis," *Nuc. Acids Res.* 19(18):4955–4962 (1991).

Kornher, J.S., and Livak, K.J., "Mutation Detecting Using Nucleotide Analogs that Alter Electrophoretic Mobility," *Nuc. Acids Res.* 17(19):7779–7784 (1989).

Landegren, U., et al., "A Ligase–Mediated Gene Detection Technique," *Science* 241:1077–1080 (1988).

Livak, K.J., et al., "Detection of Single Base Differences Using Biotinylated Nucleotides with Very Long Linker Arms," *Nuc. Acids Res.* 20(18):4831–4837 (1992).

Mayer, P., et al., "Theory of DNA Sequencing Using Free Solution Electrophoresis of Protein–DNA Complexes," *Analytical Chem.* 66:1777–1780 (1994).

Nathakarkitkool, S., et al., "High–Resolution Capillary Electrophoretic Analysis of DNA in Free Solution," *Electrophoresis* 13:18–31 (1992).

Prober, J.M., et al., "A System for Rapid DNA Sequencing with Flourescent Chain–Terminating Dideoxynucleotides," *Science* 238:336–341 (1987).

Saiki, R.K., et al., "Enzymatic Amplification of β–Globin Genomic Sequences and Restriction Site Analysis for Diagnosis of Sickle–Cell Anemia," *Science* 230:1350–1354 (1985).

Skolnick, M.H., and Wallace, R.B., "Simultaneous Analysis of Multiple Polymorphic Loci Using Amplified Sequence Polymorphisms (ASPs)," *Genomics* 2273–279 (1988).

Winn–Deen, E.S., and Iovannisci, D.M., "Sensitive Fluorescence Method for Detecting DNA Ligation Amplification Products," *Clin. Chem.* 37(9):1522–1523 (1991).

Wu, D.Y., and Wallace, R.B., "Specificity of the Nick–Closing Activity of Bacteriophage T4 DNA Ligase," *Gene* 76:245–254 (1989).

"Optimization and Troubleshooting DNA Sequencing with the Model 370A for Use with Version 1.20 Data Analysis Software," *Applied Biosystems User Bulletin* 7:1–15 (Apr. 15, 1988).

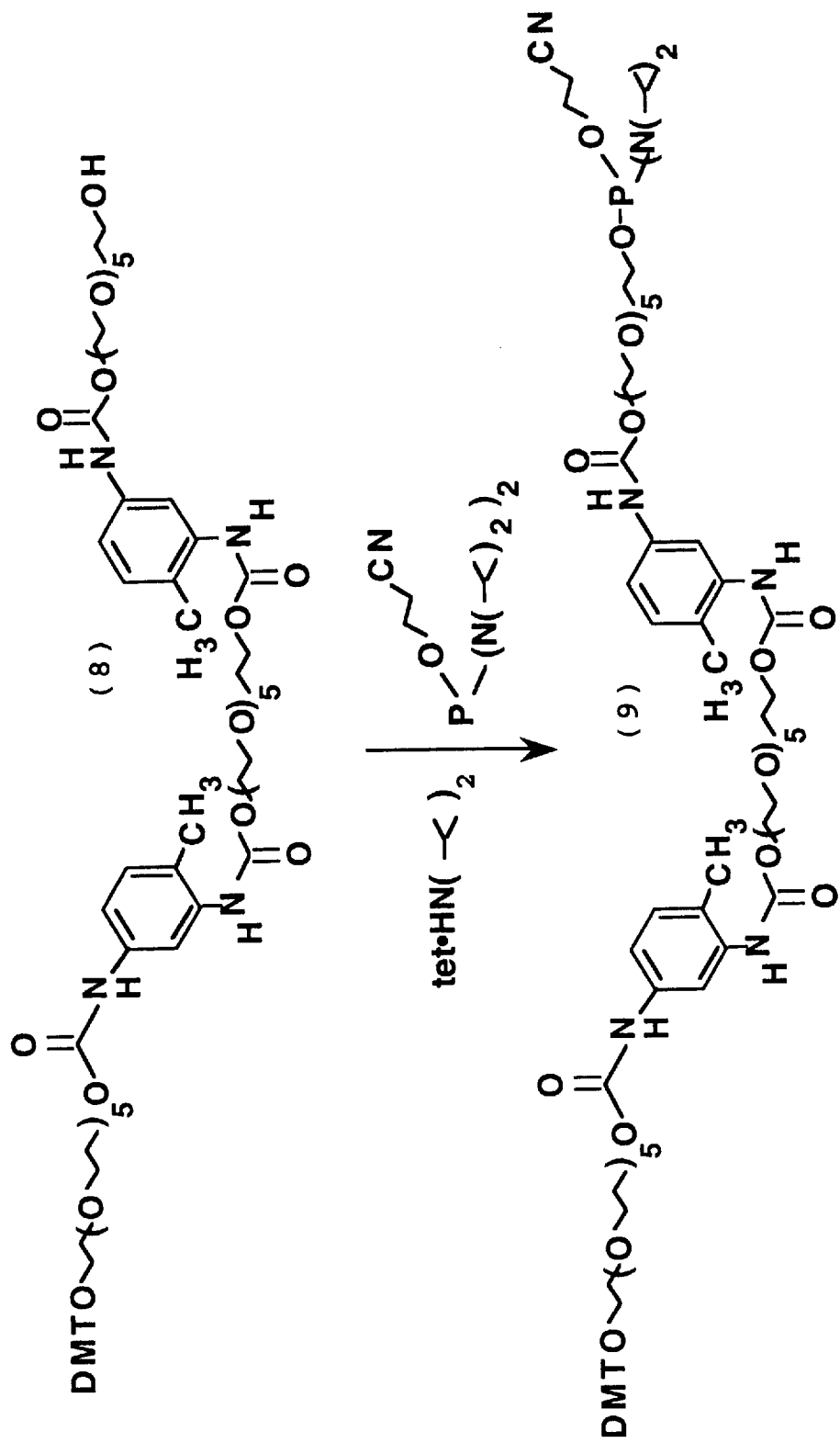
Fig. 3 (con't)

↓ PROBE COMPOSITION
↓ ANNEAL

LIGASE ↓

↓ DENATURE

↓ LIGATE

↓ DENATURE, REANNEAL

↓ LIGATE

↓ DENATURE

↓ REPEAT N-2 TIMES x $2^N$

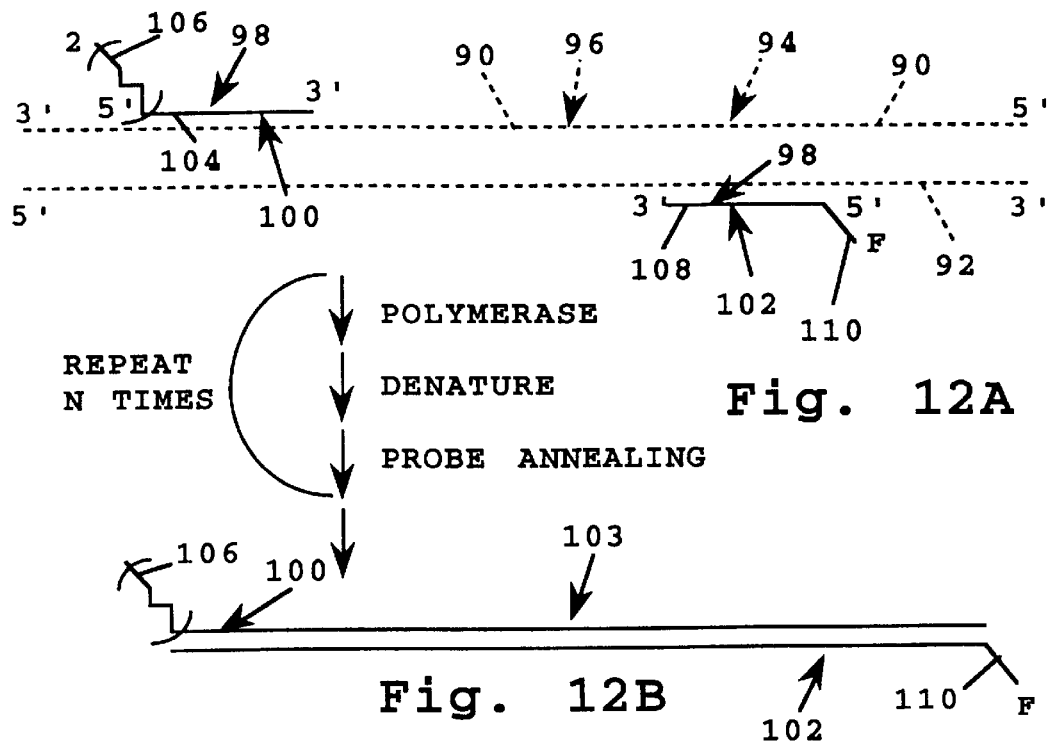
Fig. 12A
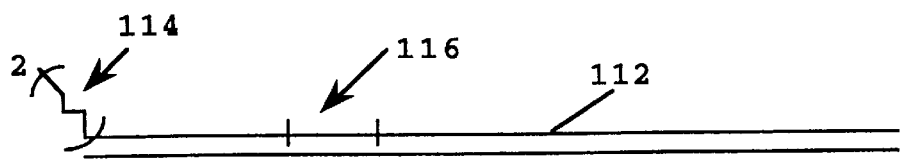
Fig. 12B
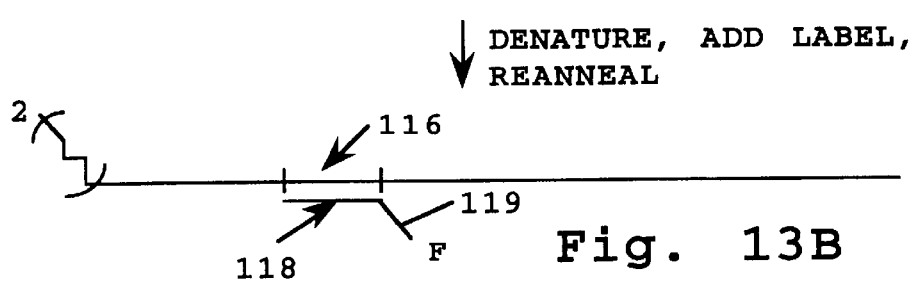
Fig. 13A
Fig. 13B
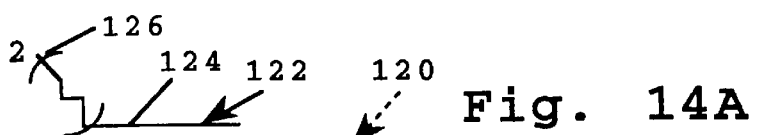
Fig. 14A
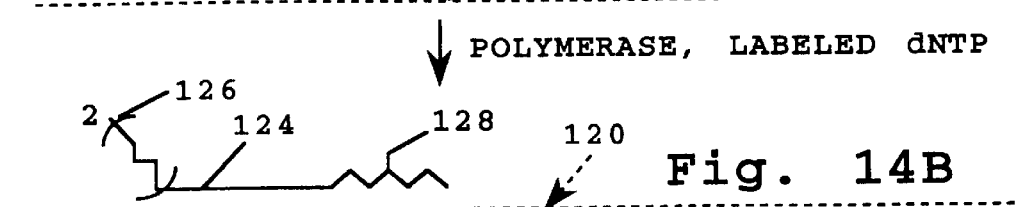
Fig. 14B ↓ RNAase H, DENATURE

↓ LIGATE, DENATURE

PROBE COMPOSITION CONTAINING A BINDING DOMAIN AND POLYMER CHAIN AND METHOD OF USE

This is a continuation of application Ser. No. 08/561,478, filed Nov. 21, 1995, U.S. Pat. No. 5,703,222, which is a continuation of application Ser. No. 07/866,018, filed Apr. 7, 1992, U.S. Pat. No. 5,470,705, which is a continuation-in-part of application Ser. No. 07/862,642 filed Apr. 3, 1992, abandoned.

FIELD OF THE INVENTION

The present invention relates to a probe composition, and to methods of using the composition for detecting selected sequences in a target polynucleotide.

REFERENCES

Applied Biosystems, DNA Sequencer User Bulletin, #11, "Synthesis of Fluorescent Dye-Labeled oligonucleotides for Use as Primers in Fluorescence-Based DNA sequencing (1989).
Blake, et al., Biochemistry, 24: 6132 (1985a).
Blake, et al., Biochemistry, 24: 6139 (1985b).
Caruthers et al., J. Am Chem Soc, 113(6324) (1991).
Cohen, A. S., et al., Anal Chem, 59(7):1021 (1987).
Connel C., et al., Biotechniques, 5(342) (1987).
Cload, S. T., et al., J Am Chem Soc, 113: 6324 (1991).
Duck, P., et al., Biotechniques, 9:142 (1989).
Froehler, et al., Nucleic Acids Res, 16:4831 (1988)
Hermans, J. J., J Polymer Sci 18(257) (1953).
Holland, et. al., Proc Nat Acad Sci, U.S.A., 88:7276 (1991).
Kornberg, A., et al., "DNA Replication", pp 46–47, W. H. Freeman and Co., New York (1992).
Landegren, U., et al., Science, 241:1077 (1988).
Miller, P. S., et al, Biochemistry, 18:5134 (1979).
Miller, P. S., et al., J Biol Chem, 255:6959 (1980).
Miller, P. S., et al., Bioconjugate Chem, 1(187) (1990).
Mullis, K., et al., U.S. Pat. No. 4,683,202 (1987).
Murakami, et al., Biochemistry, 24:4041 (1985).
Olivera, B. M., et al., Biopolymers, 2(245) (1964).
Saiki, R. K., et al., Science, 230:1350 (1985).
Sterchak, E. P., et al., Organic Chem, 52:4202 (1987).
Terabe, S., et al., et al., Anal Chem, 57(4):834 (1985).
Towns, J. K., et al, Anal Chem, 63:1126 (1991).
Whiteley, N. M., et al., U.S. Pat. No. 4,883,750 (1989).
Winn-Deen, E., et al., Clin Chem, 37: 1522 (1991).
Wu, D. Y., et al., Genomics, 4:560 (1989).

BACKGROUND OF THE INVENTION

A variety of DNA hybridization techniques are available for detecting the presence of one or more selected polynucleotide sequences in a sample containing a large number of sequence regions. In a simple method, which relies on fragment capture and labeling, a fragment containing a selected sequence is captured by hybridization to an immobilized probe. The captured fragment can be labeled by hybridization to a second probe which contains a detectable reporter moiety.

Another widely used method is Southern blotting. In this method, a mixture of DNA fragments in a sample are fractionated by gel electrophoresis, then fixed on a nitrocellulose filter. By reacting the filter with one or more labeled probes under hybridization conditions, the presence of bands containing the probe sequence can be identified. The method is especially useful for identifying fragments in a restriction-enzyme DNA digest which contain a given probe sequence, and for analyzing restriction-fragment length polymorphisms (RFLPs).

Another approach to detecting the presence of a given sequence or sequences in a polynucleotide sample involves selective amplification of the sequence(s) by polymerase chain reaction (Mullis, Saiki). In this method, primers complementary to opposite end portions of the selected sequence(s) are used to promote, in conjunction with thermal cycling, successive rounds of primer-initiated replication. The amplified sequence may be readily identified by a variety of techniques. This approach is particularly useful for detecting the presence of low-copy sequences in a polynucleotide-containing sample, e.g., for detecting pathogen sequences in a body-fluid sample.

More recently, methods of identifying known target sequences by probe ligation methods have been reported (Wu, Whiteley, Lundegren, Winn-Deen). In one approach, known as oligonucleotide ligation assay (OLA), two probes or probe elements which span a target region of interest are hybridized with the target region. Where the probe elements match (basepair with) adjacent target bases at the confronting ends of the probe elements, the two elements can be joined by ligation, e.g., by treatment with ligase. The ligated probe element is then assayed, evidencing the presence of the target sequence.

In a modification of this approach, the ligated probe elements act as a template for a pair of complementary probe elements. With continued cycles of denaturation, reannealing and ligation in the presence of the two complementary pairs of probe elements, the target sequence is amplified geometrically, i.e., exponentially allowing very small amounts of target sequence to be detected and/or amplified. This approach is also referred to as Ligase Chain Reaction (LCR).

There is a growing need, e.g., in the field of genetic screening, for methods useful in detecting the presence or absence of each of a large number of sequences in a target polynucleotide. For example, as many as 150 different mutations have been associated with cystic fibrosis. In screening for genetic predisposition to this disease, it is optimal to test all of the possible different gene sequence mutations in the subject's genomic DNA, in order to make a positive identification of a "cystic fibrosis". Ideally, one would like to test for the presence or absence of all of the possible mutation sites in a single assay.

These prior-art methods described above are not readily adaptable for use in detecting multiple selected sequences in a convenient, automated single-assay format. It is therefore desirable to provide a rapid, single-assay format for detecting the presence or absence of multiple selected sequences in a polynucleotide sample.

SUMMARY OF THE INVENTION

The present invention includes, in one aspect, a method of detecting one or more of a plurality of different sequences in a target polynucleotide. In practicing the method, there is added to the target polynucleotide, a plurality of sequence-specific probes, each characterized by (a) a binding polymer having a probe-specific sequence of subunits designed for base-specific binding of the polymer to one of the target sequences, under selected binding conditions, and (b) attached to the binding polymer, a polymer chain having a different ratio of charge/translational frictional drag from that of the binding polymer.

The probes are reacted with the target polynucleotide under conditions favoring binding of the probes in a base-specific manner to the target polynucleotide. The probes are then treated to selectively modify those probes which are bound to the target polynucleotide in a sequence-specific manner, forming modified, labeled probes characterized by (a) a distinctive ratio of charge/translational frictional drag, and (b) a detectable reporter label.

The modified, labeled probes are fractionated by electrophoresis in a non-sieving matrix. The presence of selected sequence(s) in the target polynucleotide is detected according to the observed electrophoretic migration rates of the labeled probes.

The polymer chain may be a substantially uncharged, water-soluble chain, such as a chain composed of polyethylene oxide (PEO) units or a polypeptide chain, where the chains attached to different-sequence binding polymers have different numbers of polymer units. Electrophoresis is preferably performed under conditions of efficient heat dissipation from the non-sieving medium, such as in a capillary tube.

In one general method, each probe includes first and second probe elements having first and second sequence-specific oligonucleotides which, when bound in a sequence specific manner to a selected single-stranded target sequence, have (or can be modified to have) confronting end subunits which can basepair to adjacent bases in the target polynucleotide sequence. After hybridizing the oligonucleotides to the target polynucleotide, the target-bound oligonucleotides are ligated, to join those hybridized oligonucleotides whose confronting end subunits are base-paired with adjacent target bases. In each pair of probe elements, one of the probe elements contains the probe-specific polymer chain, and the other element preferably includes a detectable reporter.

In a second general embodiment, each probe includes first and second primer elements having first and second sequence-specific oligonucleotide primers effective to hybridize with opposite end regions of complementary strands of a selected target polynucleotide segment. The first probe element contains the probe-specific polymer chain. The primer elements are reacted with the target polynucleotide in a series of primer-initiated polymerization cycles which are effective to amplify the target sequence of interest.

The amplification reaction may be carried out in the presence of reporter-labeled nucleoside triphosphates, for purposes of reporter labeling the amplified sequences. Alternatively, the amplified target sequences may be labeled, in single-stranded form, by hybridization with one or more reporter-labeled, sequence-specific probes, or in double-stranded form by covalent or non-covalent attachment of a reporter, such as ethidium bromide.

In a third general embodiment, bound oligonucleotide probes are reacted with reporter-labeled nucleoside triphosphate molecules, in the presence of a DNA polymerase, to attach reporter groups to the 3' end of the probes.

In a fourth general embodiment, each probe includes a binding polymer which is modified by enzymatic cleavage when bound to a target sequence. The cleavage reaction may remove a portion of the binding polymer, to modify the probes's ratio of charge/translational frictional drag, or may separate a reporter label carried at one end of the binding polymer from a polymer chain carried at the other end of the binding polymer, to modify the charge/translational frictional drag of the binding polymer carrying the reporter label.

In a fifth general embodiment, each sequence-specific probe includes a binding polymer and an attached reporter label, and the polymer chain associated with each different-sequence probe imparts to that probe, a distinctive ratio of charge/translational frictional drag. The treating step includes immobilizing the target polynucleotide, washing the immobilized target polynucleotide to remove probes not bound to the target polynucleotide in a sequence-specific manner, and denaturing the target polynucleotide to release probes bound in a sequence-specific manner.

Also forming part of the invention is a probe composition for use in detecting one or more of a plurality of different sequences in a target polynucleotide. The composition includes a plurality of sequence-specific probes, each characterized by (a) a binding polymer having a probe-specific sequence of subunits designed for base-specific binding of the polymer to one of the target sequences, under selected binding conditions, and (b) attached to the binding polymer, a polymer chain having a ratio of charge/translational frictional drag which is different from that of the binding polymer.

In one embodiment, each sequence specific probe further includes a second binding polymer, where the first-mentioned and second binding polymers in a sequence-specific probe are effective to bind in a base-specific manner to adjacent and contiguous regions of a selected target sequence, allowing ligation of the two binding polymers when bound to the target sequence in a sequence-specific manner. The second binding polymer preferably includes a detectable label, and the polymer chain attached to the first binding polymer imparts to each ligated probe pair, a distinctive combined ratio of charge/translational frictional drag.

In another embodiment, each sequence specific probe in the composition further includes a second binding polymer, where the first-mentioned and second binding polymers in a sequence-specific probe are effective to bind in a base-specific manner to opposite end regions of opposite strands of a selected duplex target sequence, allowing primer initiated polymerization of the target region in each strand. The second binding polymer preferably includes a detectable label, and the polymer chain attached to the first binding polymer imparts to each ligated probe pair, a distinctive combined ratio of charge/translational frictional drag.

In another embodiment, each sequence-specific probe includes a binding polymer, a polymer chain attached to the binding polymer, and a reporter attached to the binding polymer.

These and other objects and features of the invention will become more fully apparent when the following detailed description of the invention is read in conjunction with the accompanying drawings.

BRIEF DESCRIPTION OF THE DRAWINGS

FIGS. 12A–12B illustrate the steps in a second general embodiment of the invention, using primer-initiated amplification to produce double-stranded labeled probes;

FIGS. 13A and 13B illustrate an alternative method for labeling amplified target sequences formed in the FIG. 12 method;

FIGS. 14A and 14B illustrate steps in a third general embodiment of the invention, using reporter-labeled nucleotide addition to the target-bound probes to form labeled probe species;

DETAILED DESCRIPTION OF THE INVENTION

I. Definitions

"A target polynucleotide" may include one or more nucleic acid molecules, including linear or circularized single-stranded or double-stranded RNA or DNA molecules.

"Target nucleic acid sequence" means a contiguous sequence of nucleotides in the target polynucleotide. A "plurality" of such sequences includes two or more nucleic acid sequences differing in base sequence at one or more nucleotide positions.

"Sequence-specific binding polymer" means a polymer effective to bind to one target nucleic acid or sequence subset with base-sequence specificity, and which has a substantially lower binding affinity, under selected hybridization conditions, to any other target sequence or sequence subset in a given plurality of sequences in the test sample.

The "charge" of a polymer is the total net electrostatic charge of the polymer at a given pH;

The "translational frictional drag" of a polymer is a measure of the polymer's frictional drag as it moves electrophoretically through a defined, non-sieving liquid medium.

"Non-sieving matrix" means a liquid medium which is substantially free of a mesh or network or matrix of interconnected polymer molecules.

A "distinctive ratio of charge/translational frictional drag" of a probe is evidenced by a distinctive, i.e., unique, electrophoretic mobility of the probe in a non-sieving medium.

"Capillary electrophoresis" means electrophoresis in a capillary tube or in a capillary plate, where the diameter of separation column or thickness of the separation plate is between about 25–500 microns, allowing efficient heat dissipation throughout the separation medium, with consequently low thermal convection within the medium.

A "labeled probe" refers to a probe which is composed of a binding polymer effective to bind in a sequence-specific manner to a selected target sequence, a polymer chain which imparts to the binding polymer, a distinctive ratio of charge/translational frictional drag, and a detectable reporter or tag.

A "reporter" or "label" or "reporter label" refers to a fluorophore, chromophore, radioisotope, or spin label which allows direct detection of a labeled probe by a suitable detector, or a ligand, such as an antigen, or biotin, which can bind specifically and with high affinity to a detectable anti-ligand, such as a reporter-labeled antibody or avidin.

II. Probe Composition

Figure 1A:
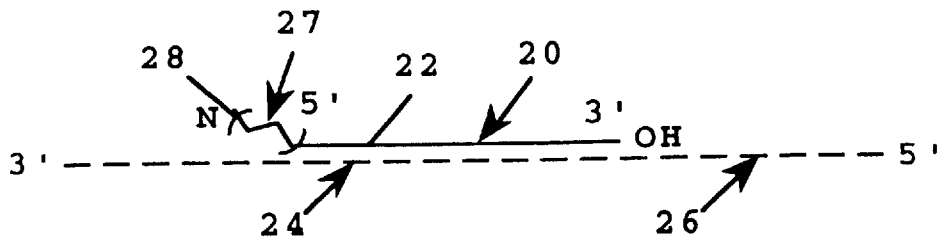
FIGS. 1A–1D illustrate three general types of probes and probe elements used in practicing various embodiments of the method of the invention.
Figure 1B:
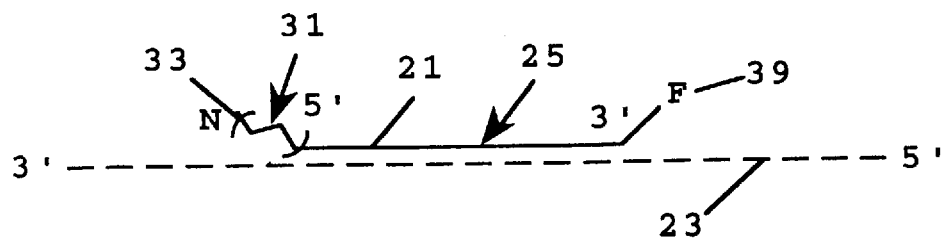
Figure 1C:
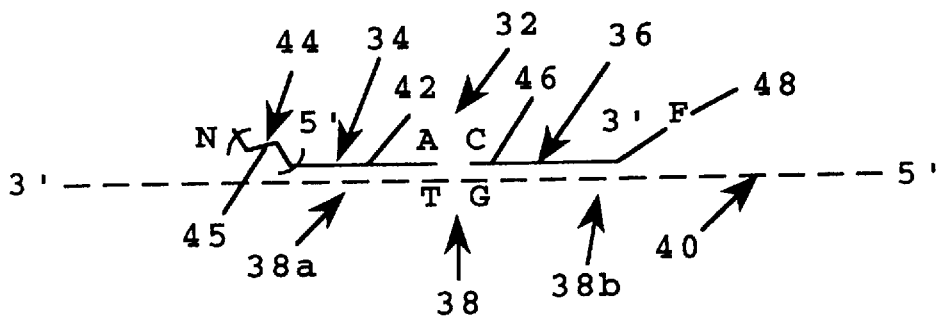

This section describes several embodiments of probes designed for use in the present invention. In the typical case, the probe is part of a probe composition which contains a plurality of probes used for detecting one or more of a plurality of target sequences, according to methods described in Section III. The probes described with reference to FIGS. 1B and 1C are representative of probes or probe elements which make up probe compositions in accordance with the present invention.

A. Probe Structure

FIG. 1 shows a probe 20 which is one of a plurality of probes used in one embodiment of the method of the invention. As will be seen below, a probe composition containing a probe like probe 20 is designed for use in a "probe-extension" method of identifying target sequences, such as the sequence in region 24 of a target polynucleotide, indicated by dashed line at 26 in FIG. 1A, or in a "probe-capture" method for identifying such target sequences. Both methods are discussed in Section IV below.

Probe 20 includes an oligonucleotide binding polymer 22 which preferably includes at least 10–20 bases, for requisite basepair specificity, and has a base sequence which is complementary to region 24 in target polynucleotide 26, with such in single-stranded form. Other probes in the composition have sequence specificities for other target regions of known sequence in the target polynucleotide. In a preferred embodiment, the binding polymers of the different-sequence probes all have about the same length, allowing hybridization of the different probes to the target polynucleotide with substantially the same hybridization reaction kinetics and thermodynamics ($T_m$).

Other binding polymers which are analogs of polynucleotides, such as deoxynucleotides with thiophosphodiester linkages, and which are capable of base-specific binding to single-stranded or double-stranded target polynucleotides are also contemplated. Polynucleotide analogs containing uncharged, but stereoisomeric methylphosphonate linkages between the deoxyribonucleoside subunits have been reported (Miller, 1979, 1980, 1990, Murakami, Blake, 1985a, 1985b). A variety of analogous uncharged phosphoramidate-linked oligonucleotide analogs have also been reported (Froehler). Also, deoxyribonucleoside analogs having achiral and uncharged intersubunit linkages (Sterchak) and uncharged morpholino-based polymers having achiral intersubunit linkages have been reported (U.S. Pat. No. 5,034,506). Such binding polymers may be designed for sequence specific binding to a single-stranded target molecule through Watson-Crick base pairing, or sequence-specific binding to a double-stranded target polynucleotide through Hoogstein binding sites in -the major groove of duplex nucleic acid (Kornberg).

The binding polymer in the probe has a given ratio of charge/translational frictional drag, as defined above, and this ratio may be substantially the same for all of the different-sequence binding polymers of the plurality of probes making up the probe composition. This is evidenced by the similar migration rates of oligonucleotides having different sizes (numbers of subunits) and sequences by electrophoresis in a non sieving medium.

The oligonucleotide binding polymer in probe 20 is derivatized, at its 5' end, with a polymer chain 27 composed of N subunits 28. The units may be the subunits of the polymer or may be groups of subunits. Exemplary polymer chains are formed of polyethylene oxide, polyglycolic acid, polylactic acid, polypeptide, oligosaccharide, polyurethane, polyamids, polysulfonamide, polysulfoxide, and block copolymers thereof, including polymers composed of units of multiple subunits linked by charged or uncharged linking groups.

According to an important feature of the invention, the polymer chain has a ratio of charge/translational frictional drag which is different from that of the binding polymer. In the method of the invention, detailed in Section IV below, the probes are treated to selectively modify those probes bound in a sequence-specific manner to a target sequence, to produce modified, labeled probes having a distinct ratio of charge/translational frictional coefficient, as evidenced by a distinctive electrophoretic mobility in a non-sieving matrix, as discussed in Section III below. As will be discussed below, the distinctive ratio of charge/translational frictional drag is typically achieved by differences in the lengths (number of subunits) of the polymer chain. However, differences in polymer chain charge are also contemplated, as are differences in binding-polymer length.

More generally, the polymers forming the polymer chain may be homopolymers, random copolymers, or block copolymers, and the polymer may have a linear, comb, branched, or dendritic architecture. In addition, although the invention is described herein with respect to a single polymer chain attached to an associated binding polymer at a single point, the invention also contemplates binding polymers which are derivatized by more than one polymer chain element, where the elements collectively form the polymer chain.

Preferred polymer chains are those which are hydrophilic, or at least sufficiently hydrophilic when bound to the oligonucleotide binding polymer to ensure that the probe is readily soluble in aqueous medium. The polymer chain should also not affect the hybridization reaction. Where the binding polymers are highly charged, as in the case of oligonucleotides, the polymer chains are preferably uncharged or have a charge/subunit density which is substantially less than that of the binding polymer.

Methods of synthesizing selected-length polymer chains, either separately or as part of a single-probe solid-phase synthetic method, are described below, along with preferred properties of the polymer chains.

Figure 2:
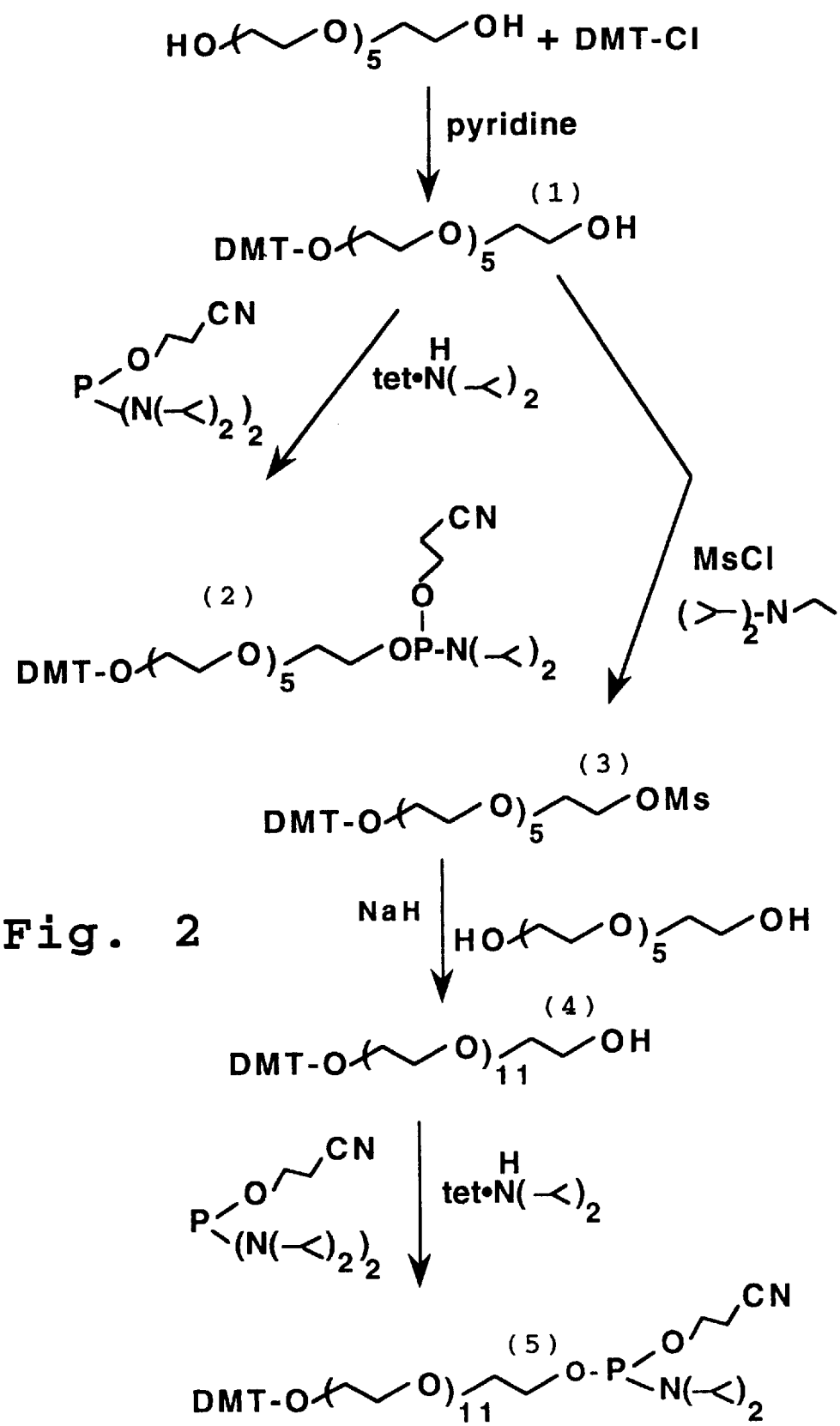
FIG. 2 illustrates methods of synthesis of polyethylene oxide polymer chains having a selected number of hexapolyethylene oxide (HEO) units.

In one preferred embodiment, described below, the polymer chain is formed of hexaethylene oxide (HEO) units, where the HEO units are joined end-to-end to form an unbroken chain of ethylene oxide subunits, as illustrated in FIG. 2, or are joined by charged (FIG. 5) or uncharged (FIG. 3) linkages, as described below. Other embodiments exemplified below include a chain composed of N 12mer PEO units, and a chain composed of N tetrapeptide units.

B. Probe Compositions

This section describes three additional probes or probe-element pairs which are useful in specific embodiments of the method of the invention and which themselves, either as single probes or as probe sets, form compositions in accordance with the invention.

FIG. 1B illustrates a probe 25 which has a sequence-specific oligonucleotide binding polymer 21 designed for sequence-specific, i.e., base-specific binding to a region of a target polynucleotide 23. By this is meant the binding polymer contains a sequence of subunits effective to form a stable duplex or triplex hybrid with the selected single-stranded or double-stranded target sequence, respectively, under defined hybridization conditions. As ill be seen with reference to FIG. 17 below, the binding polymer may contain both DNA and RNA segments. Attached to the binding polymer, at its 5' end, is a polymer chain 31 composed of N units 33, which imparts to the binding polymer a distinctive ratio of charge/translational frictional drag, as described above. The 3' end of the binding polymer is derivatized with a reporter or tag 39. In one aspect, the invention includes a composition which includes a plurality of such probes, each with a different sequence binding polymer targeted against different target regions of interest, and each with a distinctive ratio of charge/translational frictional drag imparted by the associated polymer chain.

FIG. 1C illustrates a probe 32 which consists of first and second probe elements 34, 36, is designed particularly for detecting selected sequences in each of one or more regions, such as region 38, of a target polynucleotide, indicated by dashed line 40.

In the embodiment illustrated, the sequences of interest may involve mutations, for example, point mutations, or addition or deletion type mutations involving one or a small number of bases. In a typical example, the expected site of mutation is near the midpoint of the known-sequence target region, and divides that region into two subregions. In the example shown, the mutation is a point mutation, and the expected site of the mutation is at one of the two adjacent bases T-G, with the T base defining the 5' end of a subregion 38*a*, and the adjacent G base, defining the 3' end of adjacent subregion 38*b*. As will be seen below, the probe elements are also useful for detecting a variety of other types of target sequences, e.g., sequences related to pathogens or specific genomic gene sequences.

Probe element 32, which is representative of the first robe elements in the probe composition, is composed of an oligonucleotide binding polymer element 42 which preferably includes at least 10–20 bases, for requisite basepair specificity, and has a base sequence which is complementary to a subregion 38a in the target polynucleotide. In particular, the 3' end nucleotide bases are selected for base pairing to the 5' end nucleotide bases of the corresponding subregion, e.g., the A:T matching indicated.

The oligonucleotide in the first probe element is derivatized, at its 5' end, with a polymer chain 44 composed of N preferably repeating units 45, substantially as described with respect to chain 27 formed from units 28. As described with respect to probe 20, the polymer chain in the first probe element imparts a ratio of charge/translational frictional drag which is distinctive for each sequence-specific probe element in the composition.

Second probe element 36, which is also representative of the second probe elements in the probe composition, is composed of an oligonucleotide polymer binding element 46 which preferably includes at least 10–20 bases, for requisite basepair specificity, and has a base sequence which is complementary to a subregion 38b in the target polynucleotide. In particular, the 5' end nucleotide bases are selected for base pairing to the 3' end nucleotide bases of the corresponding subregion, e.g., the C:G matching indicated.

As seen in FIG. 1C, when the two probe elements are both hybridized to their associated target regions, the confronting end subunits in the two probes, in this example the confronting A and C bases, are matched with adjacent bases, e.g., the adjacent T and G bases in the target polynucleotide. In this condition, the two probe elements may be ligated at their confronting ends, in accordance with one embodiment of the invention described below, forming a ligated probe which contains both oligonucleotide elements, and has the sequence-specific polymer chain and a reporter attached at opposite ends of the joined oligonucleotides. It will be recognized that the condition of abutting bases in the two probes can also be produced, after hybridization of the probes to a target region, by removing overlapping deoxyribonucleotides by exonuclease treatment.

The second probe element is preferably labeled, for example, at its 3' end, with detectable reporter, such as reporter F indicated at 48 in FIG. 1C. Preferably the reporter is an optical reporter, such as a fluorescent molecule which can be readily detected by an optical detection system. A number of standard fluorescent labels, such as FAM, JOE, TAMRA, and ROX, which can be detected at different excitation wavelengths, and methods of reporter attachment to oligonucleotides, have been reported (Applied Biosystems, Connell).

In one embodiment, each probe includes two second probe elements, one element having an end-subunit base sequence which can basepair with a wildtype base in the target sequence, and a second element having an end-subunit base sequence which can basepair with an expected mutation in the sequence. The two alternative elements are labeled with distinguishable reporters, allowing for positive identification of wildtype or mutation sequences in each target region, as will be described in Section III below. Alternatively, the two second probe elements (e.g., oligonucleotides) may have the same reporters, and the first probe elements have polymer chains which impart to the two probe elements, different ratios of charge/trantarget regionctional drag, allowing the two target regions to be distinguished on the basis of electrophoretic mobility.

Figure 1D:
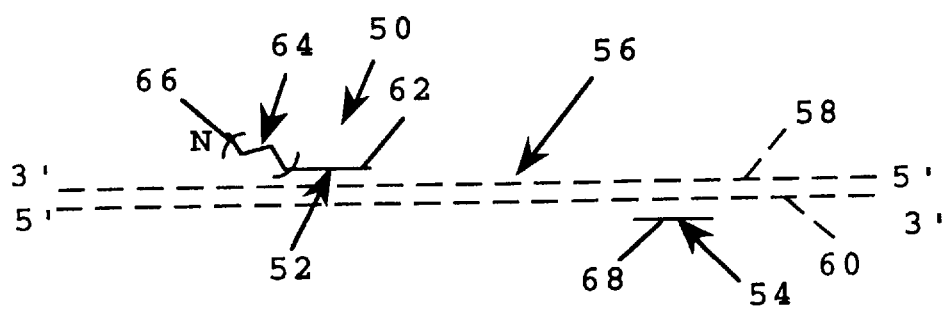

FIG. 1D shows a probe 50 which is representative of probes in a composition designed for use in another embodiment of the method of the invention. The probe, which consists of first and second primer elements 52, 54, is designed particularly for detecting the presence or absence of regions in a double-stranded target polynucleotide which are bounded by the primer-element sequences. In the example shown in FIG. 1D, the region bounded by the primer sequence is indicated at 56, and the two strands of a double-stranded target polynucleotide, by the dashed lines 58, 60.

Primer element 52, which is representative of the first primer elements in the probe composition, is composed of an oligonucleotide primer element 62 which preferably includes at least 7–15 bases, for requisite basepair specificity, and has a base sequence which is complementary to a 3'-end portion of region 56 in one of the two target strands, in this case, strand 58.

The oligonucleotide primer is derivatized, at its 5' end, with a polymer chain 64 composed of N preferably repeating units 66, substantially as described with respect to chain 27 formed from units 28. As described with respect to probe 20, the polymer chain in the first probe element imparts a ratio of charge/translational frictional drag which is distinctive for each sequence-specific primer element in the composition.

Second primer element 54, which is also representative of the second probe elements in the probe composition, is composed of an oligonucleotide primer element 68 which also preferably includes at least 7–15 bases, for requisite basepair specificity, and has a base sequence which is complementary to a 5' end portion of the opposite strand—this case, strand 60, of the duplex DNA forming region 56. The second primer element may be labeled with a detectable reporter, as described above. Alternatively, labeling can occur after formation of amplified target sequences, as described below.

C. Probe Preparation

Methods of preparing polymer chains in the probes generally follow known polymer subunit synthesis methods. Methods of forming selected-length PEO chains are discussed below, and detailed in Examples 1–4. These methods, which involve coupling of defined-size, multi-subunit polymer units to one another, either directly or through charged or uncharged linking groups, are generally applicable to a wide variety of polymers, such as polyethylene oxide, polyglycolic acid, polylactic acid, polyurethane polymers, and oligosaccharides.

The methods of polymer unit coupling are suitable for synthesizing selected-length copolymers, e.g., copolymers of polyethylene oxide units alternating with polypropylene units. Polypeptides of selected lengths and amino acid composition, either homopolymer or mixed polymer, can be synthesized by standard solid-phase methods, as outlined in Example 5.

FIG. 2 illustrates one method for preparing PEO chains having a selected number of HEO units. As shown in the figure, HEO is protected at one end with dimethoxytrityl (DMT), and activated at its other end with methane sulfonate. The activated HEO can then react with a second DMT-protected HEO group to form a DMT-protected HEO dimer. This unit-addition is carried out successively until a desired PEO chain length is achieved. Details of the method are given in Example 1.

Example 2 describes the sequential coupling of HEO units through uncharged bisurethane tolyl groups. Briefly, with respect to FIG. 3, HEO is reacted with 2 units of tolylene-2,4-diisocyanate under mild conditions, and the activated HEO is then coupled at both ends with HEO to form a bisurethane tolyl-linked trimer of HEO.

Figure 4A:
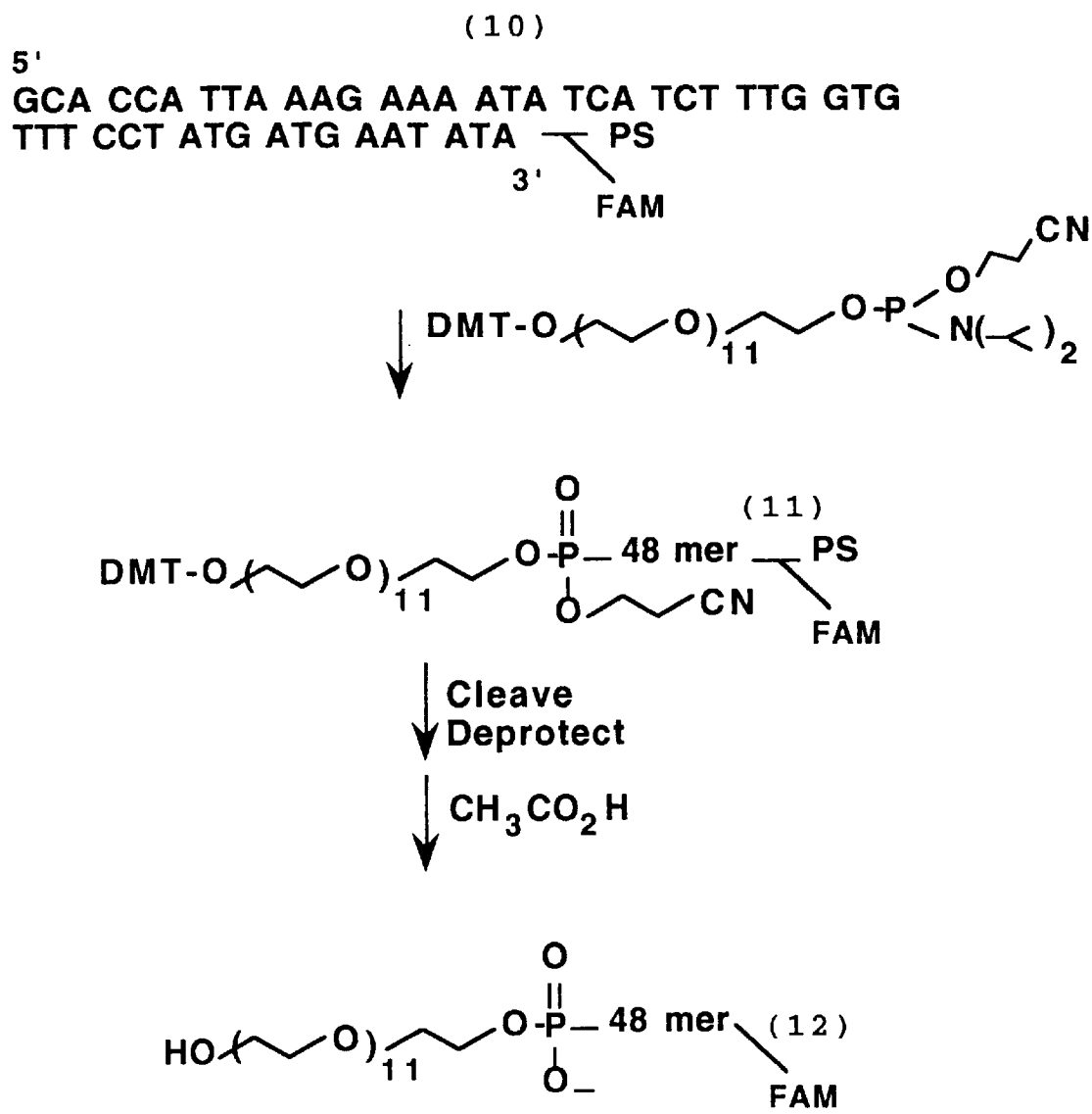
FIGS. 4A and 4B illustrate coupling reactions for coupling the polymer chains of FIGS. 2 and 3 to the 5' end of a polynucleotide, respectively; the nucleic acid sequence in FIGS. 4A and 4B is SEQ ID NO:1.
Figure 4B:
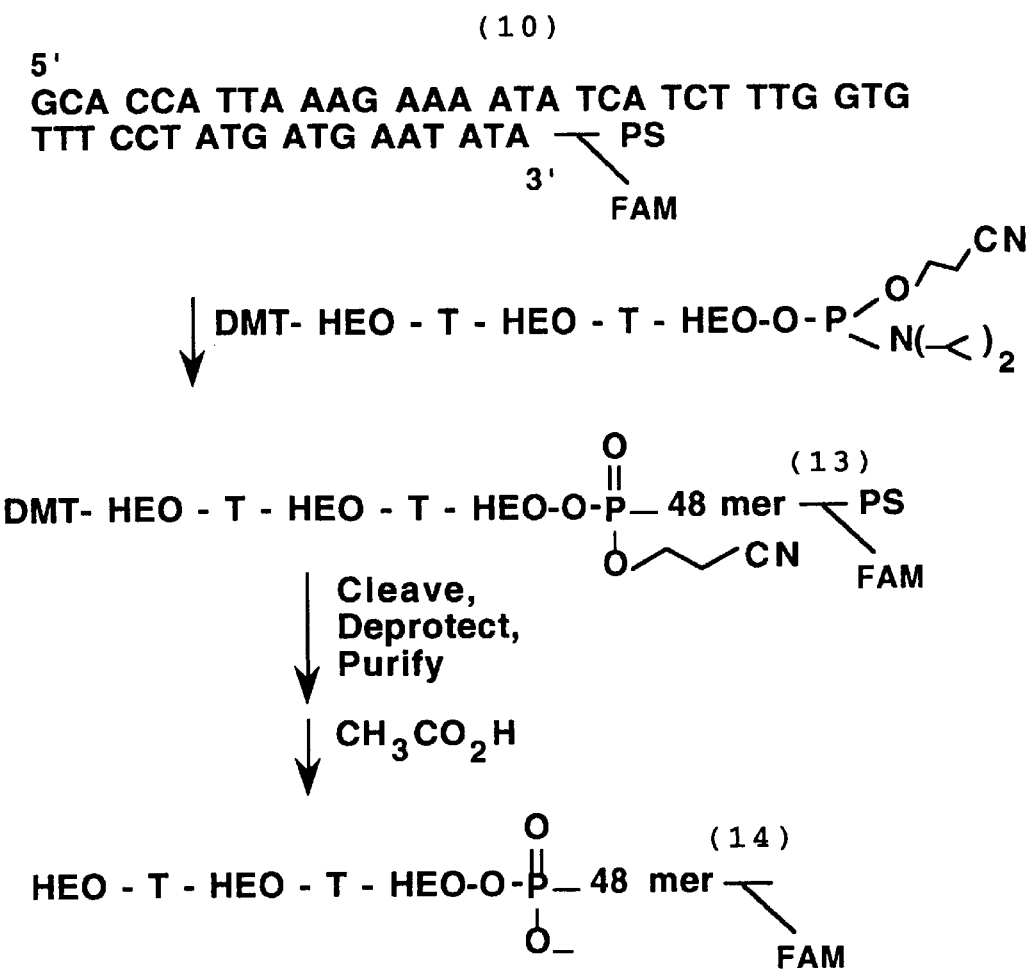

Coupling of the polymer chains to an oligonucleotide can be carried out by an extension of conventional phosphoramidite oligonucleotide synthesis methods, or by other standard coupling methods. FIG. 4A illustrates the coupling of a PEO polymer chain to the 5' end of an oligonucleotide formed on a solid support, via phosphoramidite coupling. FIG. 4B illustrates the coupling of the above bisurethane tolyl-linked polymer chain to an oligonucleotide on a solid support, also via phosphoramidite coupling. Details of the two coupling methods are given in Examples 3B and 3C, respectively.

Figure 5:
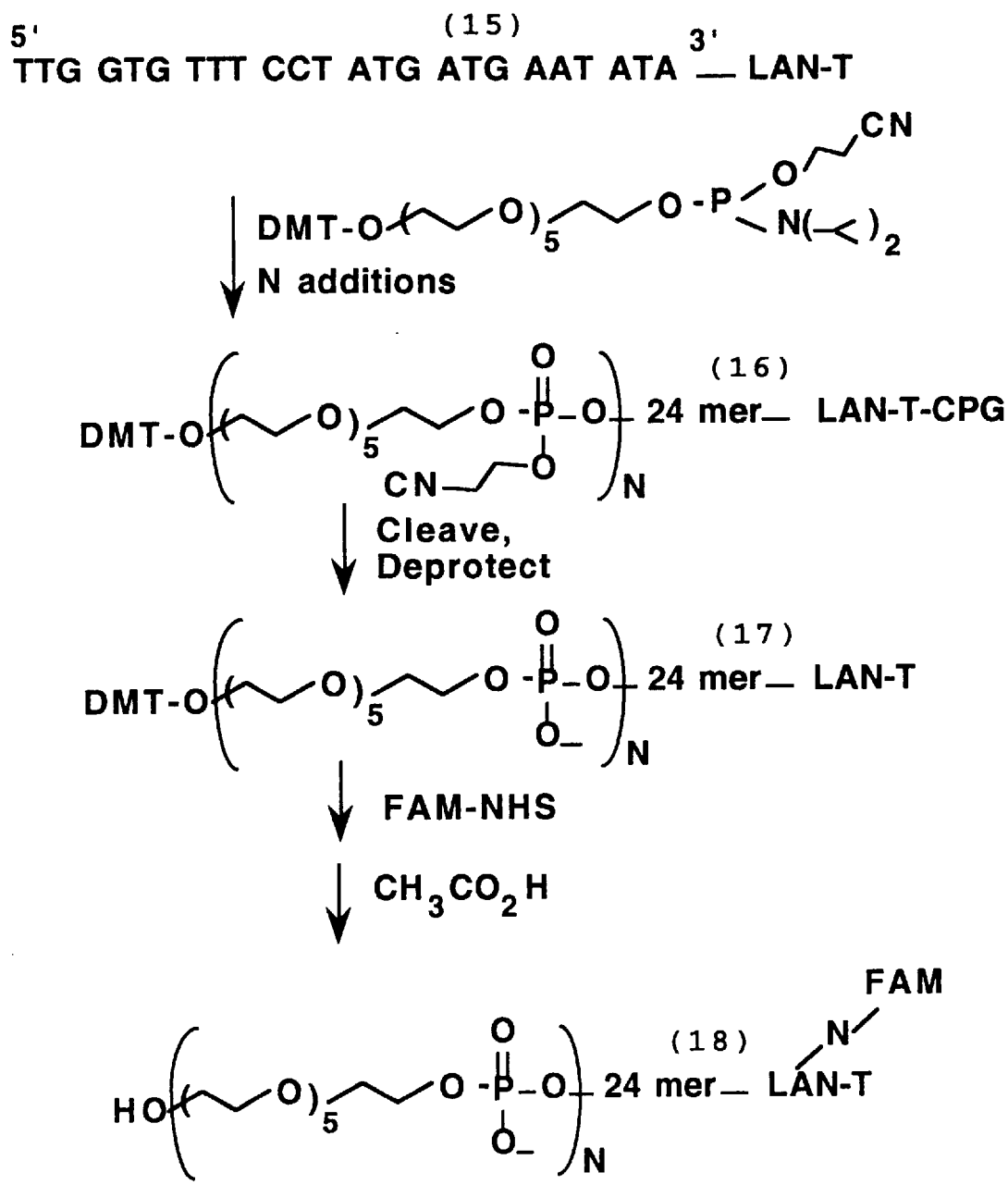
FIG. 5 shows the reaction steps for adding HEO units successively to an oligonucleotide through phosphodiester linkages, and subsequent fluorescent tagging; the nucleic acid sequence given in FIG. 5 is SEQ ID NO:2.

Alternatively, the polymer chain can be built up on an oligonucleotide (or other sequence-specific binding polymer) by stepwise addition of polymer-chain units to the oligonucleotide, using standard solid-phase synthesis methods. FIG. 5 illustrates the stepwise addition of HEO units to an oligonucleotide formed by solid-phase synthesis on a solid support. Essentially, the method follows the same phosphoramidite activation and deprotection steps used in building up the stepwise nucleotide addition. Details are given in Example 4. Example 5 describes a similar method for forming a selected-length polypeptide chain on an oligonucleotide.

As noted above, the polymer chain imparts to its probe, a ratio of charge/translational frictional drag which is distinctive for each different-sequence probe. The contribution which the polymer chain makes to the derivatized binding polymer will in general depend on the subunit length of the polymer chain. However, addition of charge groups to the polymer chain, such as charged linking groups in the PEO chain illustrated in FIG. 5, or charged amino acids in a polypeptide chain, can also be used to achieve selected charge/frictional drag characteristics in the probe.

III. Electrophoretic Separation of Labeled Probes in Non-Sieving Medium

According to an important feature of the invention, probes having different-length and/or different-sequence binding polymers, which themselves cannot be resolved by electrophoresis in a non-sieving medium, can be finely resolved by derivatization with polymer chains having slightly different size and/or charge differences.

In one preferred approach, the probes are fractionated by capillary electrophoresis in a non-sieving matrix, as defined above. The advantage of capillary electrophoresis is that efficient heat dissipation reduces or substantially eliminates thermal convection within the medium, thus improving the resolution obtainable by electrophoresis.

Electrophoresis, such as capillary electrophoresis, (CE) is carried out by standard methods, and using conventional CE equipment, except that the electrophoresis medium itself does not contain a sieving matrix. The CE protocol described in Example 6 is exemplary.

Figure 6:
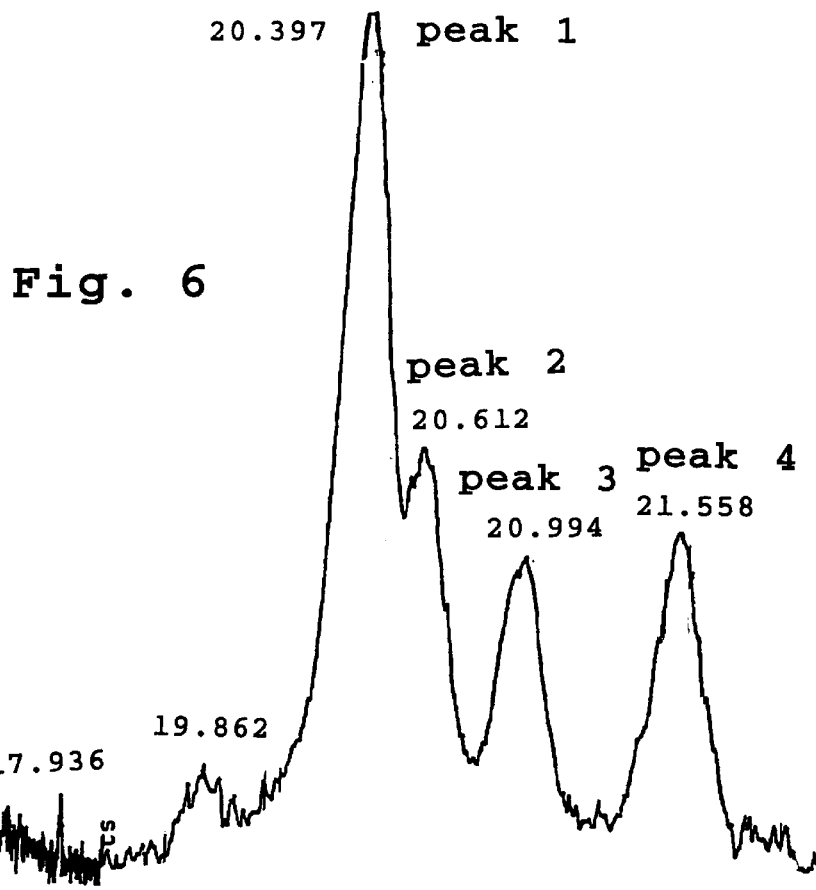
FIG. 6 is an electropherogram, on capillary electrophoresis in a non-sieving medium, of a 24 base oligonucleotide before (peak 1) and after derivatization with 1 (peak 2), 2 (peak 3), and 4 (peak 4) units of a hexaethylene oxide (HEO) unit.

FIG. 6 shows an electropherogram of fluorescent-labeled 24-base oligonucleotide probes which are either underivatized (peak 1), or derivatized at their 5' ends with a 1, 2, or 4 phosphate-linked HEO subunits (peaks 2, 3, and 4, respectively). The probes were prepared as described in Example 4, and capillary electrophoresis was carried out in a buffer medium under the conditions detailed in Example 6.

As seen in the figure, the probes are well resolved into four peaks, with migration times of 20.397, 20.612, 20.994, and 21.558 minutes. In the absence of the polymer chains, the four oligonucleotide probes would migrate at the same or substantially the same electrophoretic migration rate, i.e., would tend to run in a single unresolved peak. (This would be true whether or not the oligonucleotides had the same or different sizes (Olivera, Hermans)).

The ability to fractionate charged binding polymers, such as oligonucleotides, by electrophoresis in the absence of a sieving matrix offers a number of advantages. One of these is the ability to fractionate charged polymers all having about the same size. As will be appreciated in Section IV below, this feature allows the probes in the probe composition to have similar sizes, and thus similar hybridization kinetics and thermodynamics ($T_m$) with the target polynucleotide. Another advantage is the greater convenience of electrophoresis, particularly CE, where sieving polymers and particularly problems of forming and removing crosslinked gels in a capillary tube are avoided.

IV. Assay Method

In one aspect, the method of the invention is designed for detecting one or more different-sequence regions in a target polynucleotide. The method includes first adding to the target polynucleotide, a plurality of sequence-specific probes of the type described above. The probes are reacted with the target polynucleotide under conditions which favor sequence-specific binding of the probes to corresponding sequences in the target polynucleotide. As indicated above, this binding typically involves hybridization of complementary base sequences in the target and probe by Watson-Crick base pairing.

Alternatively, base-specific hydrogen-bond pairing between a single-strand probe and double-stranded target sequences, via Hoogstein base pairing, typically in the major groove of the duplex molecule (Kornberg), is also contemplated.

Following probe binding to the target polynucleotide, the probes are treated to selectively modify probes bound to the target sequences in a sequence-specific manner, to produce modified labeled probes, each having a distinctive charge/translational frictional drag ratio. This modifying step may involve joining probe elements by ligation, such as enzymatic ligation, across an expected mutation site, primer-initiated amplification of selected target sequences, probe extension in the presence of labeled nucleoside triphosphate molecules, enzymatic cleavage of a probe bound to a target region, or probe capture on an immobilized target, as detailed in Subsections A–E below.

The labeled probes produced by selective modification of target-bound probes are fractionated by electrophoresis in a non-sieving medium, as discussed in Section III above. The migration rates of the modified, labeled probes can be used to identify the particular sequence associated with the labeled probes, to identify the presence of particular sequences in the target polynucleotide.

A. Probe-Ligation Method

This embodiment is designed especially for detecting specific sequences in one or more regions of a target polynucleotide. The target polynucleotide may be a single molecule of double-stranded or single-stranded polynucleotide, such as a length of genomic DNA, CDNA or viral genome including RNA, or a mixture of polynucleotide fragments, such as genomic DNA fragments or a mixture of viral and somatic polynucleotide fragments from an infected sample. Typically, in the present embodiment, the target polynucleotide is double-stranded DNA which is denatured, e.g., by heating, to form single-stranded target molecules capable of hybridizing with probe binding polymers.

Figure 7A:
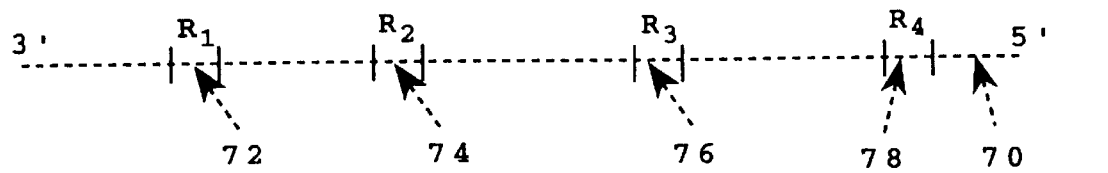
FIGS. 7A–7D illustrate a probe-ligation method of identifying target sequences, in accordance with a first general embodiment of the method of the invention.

FIG. 7A shows a portion of a single-stranded target polynucleotide 70, e.g., the "+" strand of a double-stranded target, with the 3' to 5' orientation shown. The polynucleotide contains a plurality of regions $R_1$, $R_2$, $R_3$ to $R_n$, indicated at 72, 74, 76, and 78, respectively, which each contain a different base sequence. Each region preferably has about the same length, i.e., number of basepairs, preferably between about 20–80 basepairs. The total number of regions $R_n$ which are to be assayed in the method may be up to one hundred or more, although the method is also applicable where only a few different-sequence regions are to be detected.

Although the method is illustrated in FIG. 7 with respect to a point mutation, it will be appreciated how other types of small mutational events, such as deletion or addition of one or more bases, can be detected by the method. More generally, the method can be used to assay, simultaneously, target sequences, such as sequences associated with a mixture of pathogen specimens, or gene sequences in a genomic DNA fragment mixture.

Figure 7B:
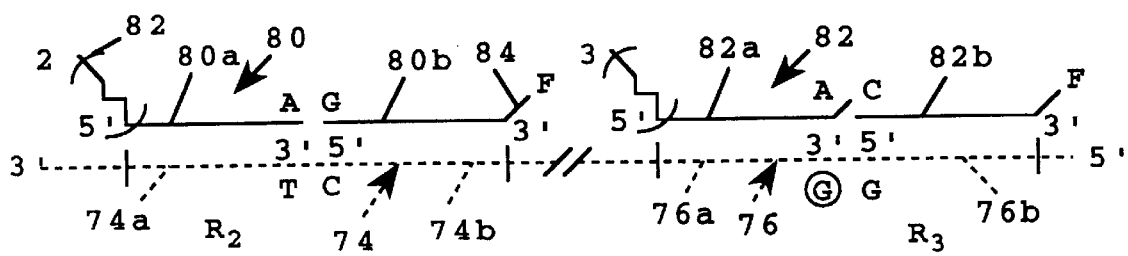
Figure 7C:
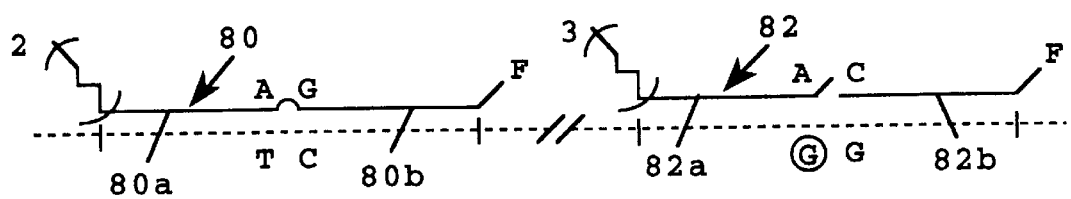

FIG. 7B shows an enlarged portion of target polynucleotide 70 which includes regions 74 ($R_2$) and 76 ($R_3$). Region 74 includes adjacent bases T and C, as shown which divide the region into two subregions 74a, 74b terminating at these two bases. The T and C bases are wildtype (non-mutated) bases, but one of these bases, e.g., the T base, corresponds to a known point-mutation site of interest. Similarly, region 76 includes adjacent bases G and G which divide this region into two subregions 76a, 76b terminating at these two bases. The G base in subregion 76a represents a point mutation from a wildtype T base, and the adjacent G base is non-mutated. The assay method is designed to identify regions of the target, such as regions 74 and/or 76, which contain such point mutations.

The probe composition used in the assay method is composed of a plurality of probe elements, such as those described with respect to FIG. 1B above. This composition is added to the target polynucleotide, with such in a denatured form, and the components are annealed to hybridize the probe elements to the complementary-sequence target regions, as shown in FIG. 1B.

One of the probes in the composition, indicated at 80, includes a pair of probe elements 80a, 80b whose sequence are complementary to the corresponding subregions 74a, 74b, respectively in region 74 of the target polynucleotide i.e., the probe element sequences correspond to those of the "−" strand of the $R_2$ region of the target. In particular, the probe elements have end-subunits A and G bases which, when the elements are hybridized to complementary subregions of region 74, as shown, are effective to form Watson-Crick base pairing with adjacent bases T and C in the target region.

Another of the probes in the composition, indicated at 82, includes a pair of probe elements 82a, 82b whose sequence are complementary to the corresponding subregions 76a, 76b, respectively in region 76 of the target polynucleotide. In this case, the probe elements have end-subunits A and C bases which, when the elements are hybridized to complementary subregions of region 76, as shown, are effective to form Watson-Crick base pairing with adjacent bases T and G bases in the wildtype target region. However, in the example shown, a T to G mutation prevents Watson-Crick base pairing of the A end-subunit to the associated target base.

Following annealing of the probe elements to corresponding target sequences, the reaction mixture is treated with ligating reagent, preferably a ligase enzyme, to ligate pairs of probe elements whose confronting bases are base-paired with adjacent target bases. Typical ligation reaction conditions are given in Example 7A. The ligation reaction is selective for those probe elements whose end subunits are base-paired with the target bases. Thus, in the example illustrated, the probe elements 80a, 80b are ligated, but probe elements 82a, 82b are not.

It can be appreciated that the ligation reaction joins an oligonucleotide carrying a sequence-specific polymer chain to an oligonucleotide carrying a detectable reporter, selectively forming modified, labeled probes, such as probe 84, composed of an oligonucleotide labeled at one end with a probe-specific polymer chain and at its other end with a detectable (fluorescent) reporter.

Figure 7D:
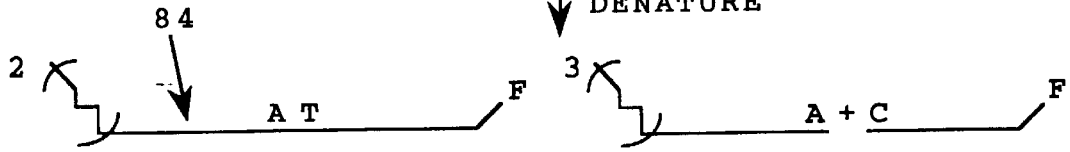

Denaturing the target-probe complexes, as illustrated in FIG. 7D, releases a mixture of ligated, labeled probes, corresponding to wildtype target sequences, and non-ligated probe elements corresponding to point mutations at or near probe element end subunits. Each ligated, labeled probe has a polymer chain which imparts to that probe, a distinctive ratio of charge/translational frictional drag, as discussed above.

Figure 8:
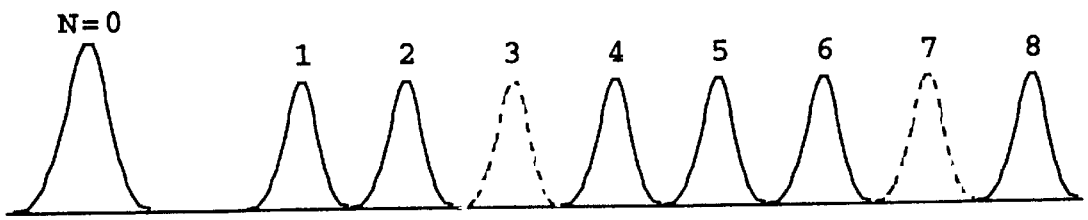
FIG. 8 illustrates an idealized electrophoretic pattern observed in the FIG. 7 method, where a target polynucleotide contains mutations in two different target regions.

In the assay method illustrated in FIGS. 7A–7D, one of the target regions ($R_3$) contains a mutation which prevents ligation of the complementary-sequence probe elements. It is assumed, by way of example, that the entire target polynucleotide contains eight sequence regions of interest, of which regions $R_3$ and $R_7$ have mutations of the type which prevent probe-element ligation, and the other six regions are wildtype sequences which lead to ligated, labeled probes. FIG. 8 shows an idealized electrophoretic pattern which would be expected in the ligation assay method. Peaks 1–8 in the figure are the expected migration times of ligated oligonucleotide probes having increasingly longer polymer chains, such as 1, 2, 3, 4, 5, 6, 7, and 8 linked HEO units. The observed electrophoretic pattern will show gaps at the 3 and 7 peak positions, as indicated, evidencing mutations in the 3 and 7 target positions. All unmodified DNA will elute substantially with the N=0 peak.

Example 7 illustrates the general principles of probe ligation and separation, in accordance with this aspect of the invention. In this method, a 25-base oligonucleotide derivatized with 1 or 2 Phe-Ala-Phe-Ala (SEQ ID NO:4) tetrapeptide units and a fluorescent-labeled 25-base oligonucleotide were mixed under hybridization conditions with a target polynucleotide whose sequence spanned the two oligonucleotides. The hybridized probe elements were treated with ligase, to form fluorescent-labeled probes carrying 1 or 2 tetrapeptide units.

Figure 9:
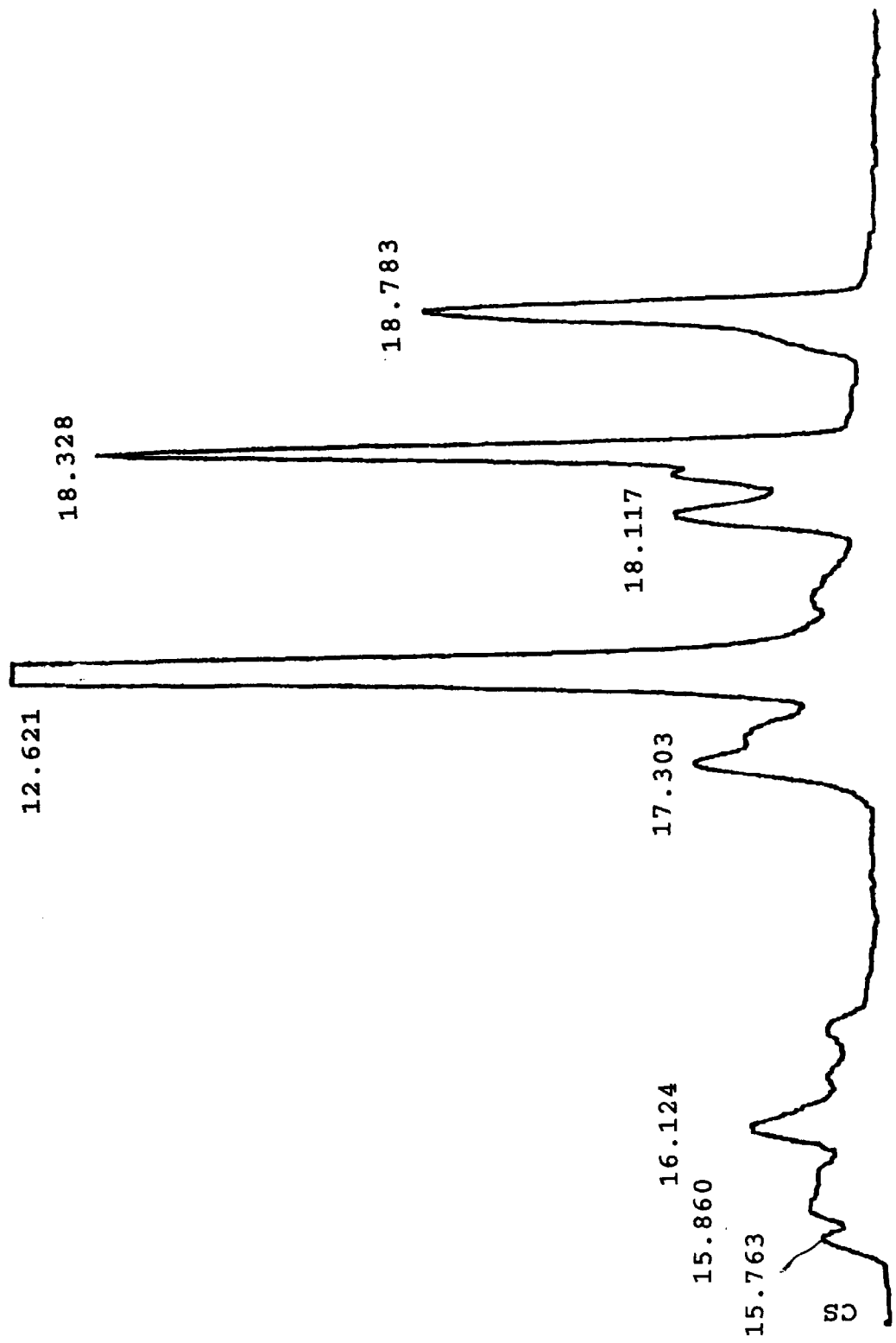
FIG. 9 is an electropherogram, on capillary electrophoresis, in a non-sieving medium, of labeled probes having polypeptide polymer chains, and formed by ligation of adjacent probes on a target molecule.

Capillary electrophoresis in a non-sieving, denaturing medium was carried out substantially as described above, and as detailed in Example 7. FIG. 9 shows the electropherogram of the fluorescent-labeled probe before ligation (peak 12,621), and the same probe when ligated with a probe containing 4-, or 8-amino acid polymer chain. As seen, the two ligated probes (peaks 18.328 and 18.783) and the unligated probe (peak 12.621) are easily resolved by CE in a non-sieving medium.

In the above OLA ligation method, the concentration of probe can be enhanced, if necessary, by amplification of the derivatized probes with repeated probe element hybridization and ligation steps. Simple additive amplification can be achieved using the target polynucleotide as a target and repeating the denaturation, annealing, and probe-element ligation steps until a desired concentration of derivatized probe is reached.

Figure 10A:
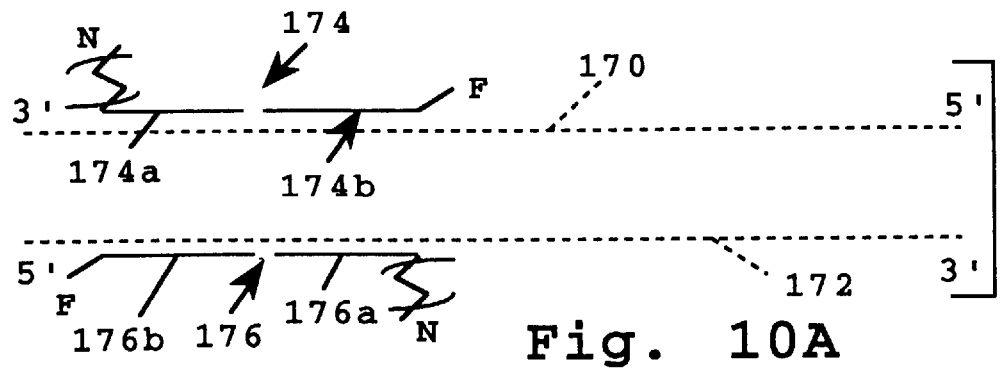
FIGS. 10A–10C illustrate a method of detecting target sequences by ligation of base-matched probes by ligase chain reaction (LCR) in accordance with the first general embodiment of the invention.

Alternatively, the ligated probes formed by target hybridization and ligation can be amplified by ligase chain reaction (LCR), according to published methods (Winn-Deen), and also as described in Example 8. In this method, illustrated in FIGS. 10A–10C, two sets of sequence-specific probes, such as described with respect to FIG. 1B, are employed for each target region of a double-stranded DNA, whose two strands are indicated at 170 and 172 in FIG. 10A. One probe set, indicated at 174, includes probe elements 174a, 174b which are designed for sequence specific binding at adjacent, contiguous regions of a target sequence on strand 170, as indicated, and a second probe set, indicated at 176, includes probe elements 176a, 176b which are designed sequence specific binding at adjacent, contiguous regions of a target sequence on opposite strand 172, also as shown.

Figure 10B:
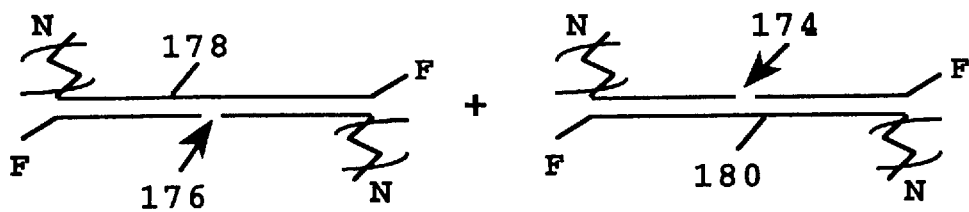
Figure 10C:
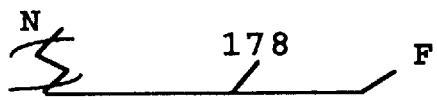
Figure 10C:
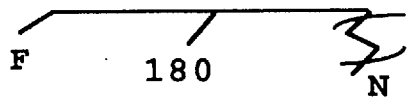

As seen, probe elements 174a and 176a are derivatized with a polymer chain, and probe elements 174b, 176b, with a fluorescent reporter, analogous to probe set 32 described above with respect to FIG. 1B. After hybridization of the two probe sets to the denatured single-stranded target sequences, the probe elements bound to each target region are ligated, and the reaction products are denatured to release labeled probes 178, 180 (FIG. 10B). These labeled probes can now serve as target substrates for binding of probe sets 174, 176, as shown in FIG. 10B, with ligation now producing $2^2$ labeled probes. This process is repeated, i.e., N−2 times, to produce ideally a total of $2^N$ labeled probes 178, 180, as indicated in FIG. 10C.

In the method described in Example 8 two pairs of probe elements were prepared, one set containing a first probe which is derivatized with a polymer chain containing either 2 or 4 dodeca ethylene oxide (DEO) units, as above, and a second probe which is labeled with a fluorescence reporter (JOE). The pairs of probe elements were targeted against the F508 region of the cystic fibrosis gene.

Figure 11:
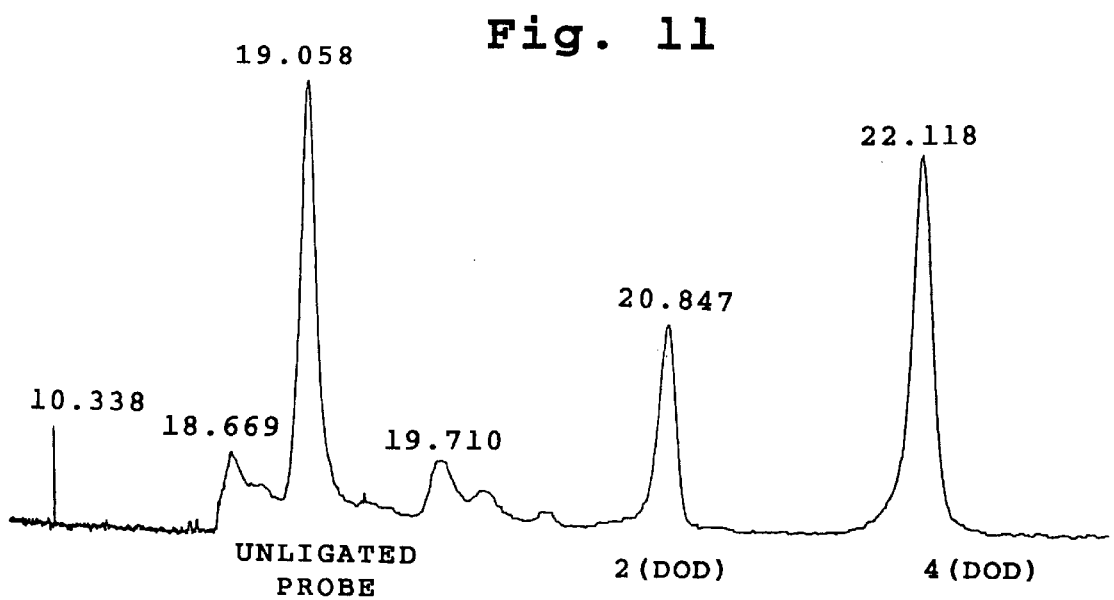
FIG. 11 is an electropherogram, on capillary electrophoresis in a non-sieving matrix, of labeled probes having polyethylene oxide polymer chains, and formed by LCR reaction.

After 30 LCR cycles, DNA from the two reaction mixtures was combined and the amplified, ligated probes in the mixture were fractionated by CE in a non-sieving buffer under denaturing conditions (8M urea). The electropherogram is shown in FIG. 11. Here the peak at the left (peak 19.058) is the unligated JOE-labeled probe. The peaks at 20.847 and 22.118 are the ligated, amplified probes containing either two or four DEO unit chains, respectively. As seen, the two probes having different length polymer chains are well resolved from one another and from probes lacking a polymer chain in a non-sieving matrix.

Although the probe-ligation method has been described above with respect to detecting mutations in each of a plurality of target regions, it is understood that the method is also applicable to detecting multiple target sequences related, for example, to the presence or absence of different pathogen sequences, or different genomic sequences in a higher organism.

Figure 18A:
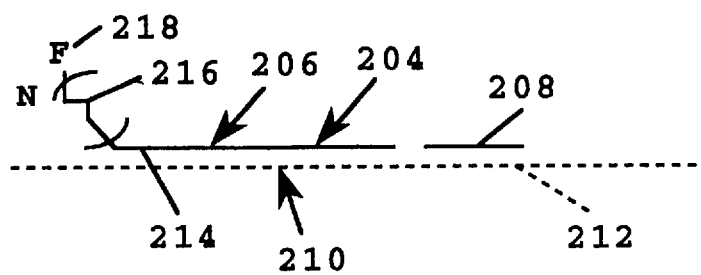
FIGS. 18A–18B illustrate an alternative probe-ligation method, in accordance with the first general embodiment of the invention.
Figure 18B:
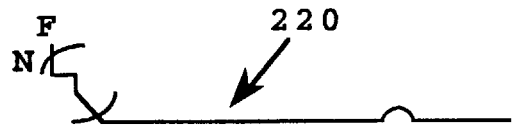

A modification of this general method is illustrated in FIGS. 18A and 18B. In this method, each sequence specific probe, such as probe 204, includes a pair of probe elements, such as elements 206, 208, which are designed for binding to adjacent portions of selected sequence, such as sequence 210 in a target polynucleotide 212. Probe 206 includes a binding polymer 214, a polymer chain 216 which imparts a distinctive charge/translational frictional drag to the probe element, and a reporter 218 which may be attached to the polymer chain or binding polymer. The second probe element is an oligonucleotide which is ligatable with probe element 206, when the two elements are hybridized to the associated target sequence, as described above with respect to FIGS. 7A–7D.

The probes are hybridized to the target polynucleotide, ligated, and released, as described above, to yield a modified labeled probe 220 whose charge/translational frictional drag ratio has been modified by virtue of the different ratio of polynucleotide/polymer chain contributions to the probe after ligation. The modified probes are then fractionated by electrophoresis in a non-sieving medium, as above, to identify probes associated with different target sequences of interest.

It will be appreciated that ligation of two oligonucleotides, in the absence of polymer chain, will not alter the electrophoretic mobility of the probe in a non-sieving matrix, since the charge/translational frictional drag of the probe remains substantially unaffected by polymer length. In the present case, however, the different contributions of the polymer chain and binding polymer to the combined charge and translational frictional drag of the probe make this ratio sensitive to the length of the binding polymer.

Figure 15A:
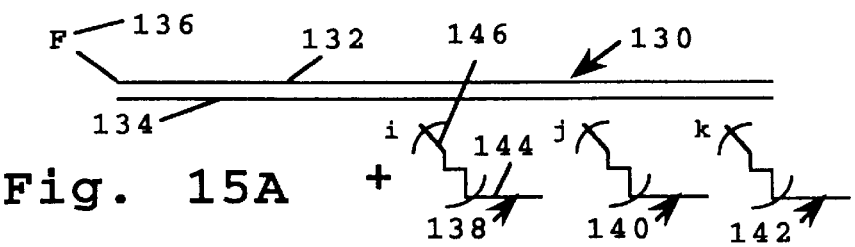
FIGS. 15A and 15B illustrate a method for labeling target duplex fragments with polymer chains, for purposes of identifying fragments containing selected sequences, in accordance with the second general embodiment of the method of the invention.
Figure 15B:
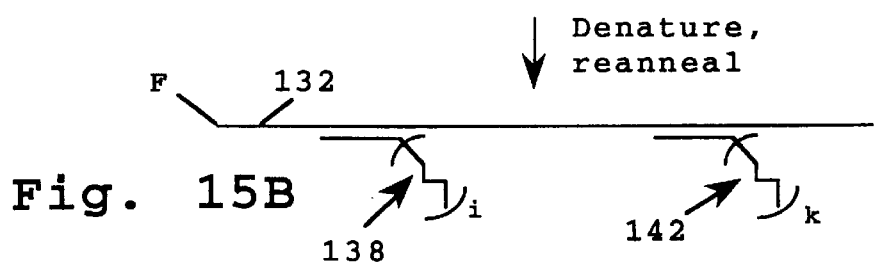
Figure 16A:
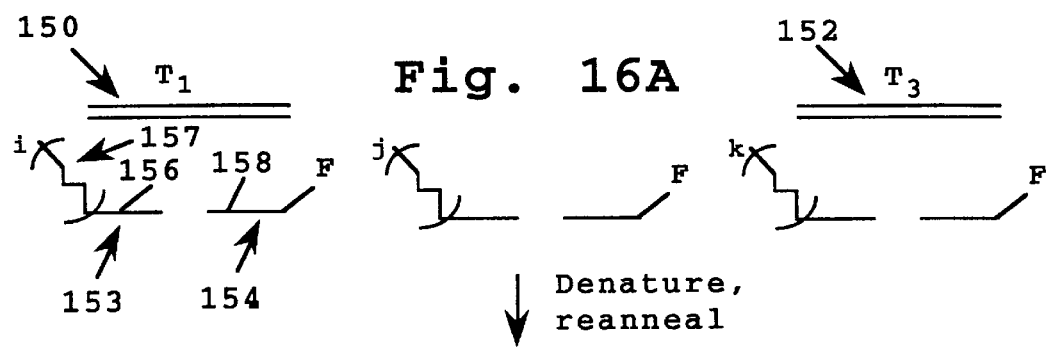
FIGS. 16A–16C illustrate an alternative method for modifying probes in a sequence specific manner to contain both polymer chains and reporter labels, in accordance with the first general embodiment of the method of the invention.
Figure 16B:
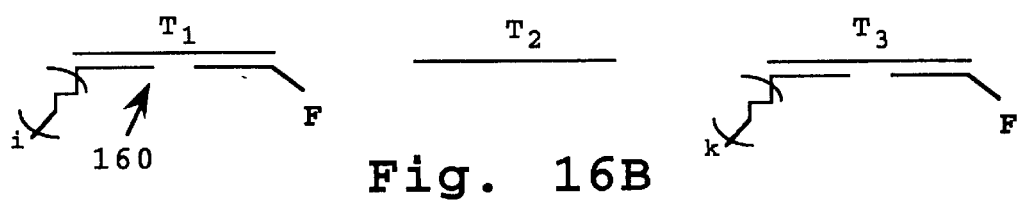
Figure 16C:
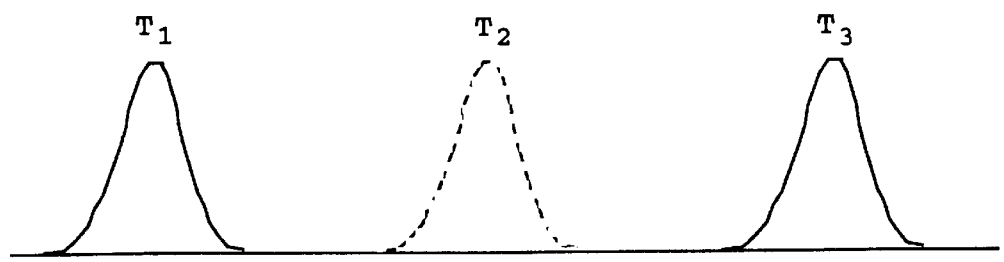

FIGS. 15A–15B illustrates a related method for modifying polynucleotide probes, in accordance with the invention. The method here is used to detect the presence of one or more sequences $S_1$ to $S_n$ associated with fragments $T_1$ to $T_n$, such as double-stranded fragments $T_1$ and $T_3$ shown at 150, 152, respectively. The fragments are modified in this method by hybridizing with a probe composition which includes, for each target sequence of interest, a pair of probe elements, such as probe elements 152, 154 which have the general construction of the probe elements described in FIG. 1B. That is, the element 152 includes an oligonucleotide 156 designed for base specific binding to one region of fragment $T_1$, and a selected length polymer chain 157, and element 154 is a reporter-labeled oligonucleotide 158 designed for base-specific binding to a second region of the fragment.

In the method, the fragments are modified by hybridization, in single-stranded form, with the probe elements in the probe composition forming fragments, such as fragment 160, with one probe having a selected-length polymer chain and a second reporter-labeled probe. The target fragment may be thought of in this method as serving a probe-ligating function to join the two probe elements. Since the fragment itself does not appreciably change the electrophoretic mobility of the joined probe elements, when fractionated by electrophoresis, the method allows for identification of target sequence fragments according to the distinctive ratio of charge/frictional drag imparted by the polymer chain in one of the probe elements.

B. Target-Sequence Amplification

In a second general embodiment of the method, illustrated in FIG. 12, the probes are designed for primer-initiated amplification of one or more regions of the double-stranded target polynucleotide. At least one strand of the amplified target regions carries a polymer chain which imparts to each amplified fragment, a distinctive ratio of charge/translational frictional drag. The amplified regions may be reporter-labeled during or after amplification.

FIGS. 12A and 12B illustrate the method. The figure shows the two separate strands 90, 92 of a normally double-stranded target polynucleotide 94 having at least one, and typically a plurality of regions, such as region 96, to be amplified. The target is reacted with a probe composition whose probes each consist of a pair of primer elements, such as primer elements 52, 54, in probe 50 described above with respect to FIG. 1C. FIG. 12A shows a probe 98 composed of primer elements 100, 102. Primer element 100 consists of an oligonucleotide primer 104 designed for hybridization to a 3' end of one strand of region 96, which carries at its 5'-end, a selected-length polymer chain 106, similar to above-describe primer element 52. Element 102 is an oligonucleotide primer designed for hybridization to a 5' end of the opposite strand region 96, which carries a fluorescent reporter at its 5'-end.

In practicing this embodiment of the method, the probe composition is reacted with the target polynucleotide under hybridization conditions which favor annealing of the primer elements in the probe composition to complementary regions of opposite target polynucleotide strands, as illustrated in FIG. 12A. The reaction mixture is then thermal cycled through several, and typically about 20–40, rounds of primer extension, denaturation, primer/target sequence annealing, according to well-known polymerase chain reaction (PCR) methods (Mullis, Saiki). One amplified region, generated by the probe primers 100, 102, is shown at 100 in FIG. 12B.

If, as in the example illustrated, one of the primers is reporter-labeled, the double-stranded amplified region, such as region 103, forms a modified, labeled probe having a polymer chain carried on one strand and a reporter on the other strand, where the polymer chain imparts to the duplex structure, a distinctive ratio of charge/translational frictional drag.

Alternatively, the amplified sequences may be labeled in double-stranded form by addition of an intercalating or cross-linking dye, such as ethidium bromide. The different-sequence amplified probes can be fractionated in double-stranded form by electrophoresis as described above, based on the different ratios of charge/translational frictional drag of the double-stranded species.

In another approach, one of the two primer elements may contain both a polymer chain and reporter label, whereby the primer-initiated polymerase reaction produces modified, labeled single-stranded probes.

The just-described method is useful, for example, in assaying for the presence of selected sequences in a target polynucleotide. As an example, the target polynucleotide may be genomic DNA with a number of possible linked gene sequences. The probes in the composition are primer pairs effective in PCR amplification of the linked sequences of interest. After sequence amplification, the presence or absence of the sequences of interest can be determined from the electrophoretic migration positions of the labeled probes.

In another application, it may be desired to assay which of a number of possible primer sequences, e.g., degenerate sequences, is complementary to a gene sequence of interest. In this application, the probe composition is used to amplify a particular sequence. Since each primer sequence will have a distinctive polymer chain, the primer sequence complementary to the sequence end regions can be determined from the migration characteristics of labeled probes. As with the other applications discussed above, the method may involve including in the fractionated probe mixture, a series of oligonucleotides derivatized with polymer chains of known sizes, and labeled different reporters groups that are carried on the test probes, to provide migration-rate standards for the electrophoretic separation.

In still another application, the amplified target fragments are labeled by hybridizing to the amplified sequences, with such in single-stranded form, a reporter-labeled probe. This application is illustrated in FIGS. 13A and 13B, which show an amplified target sequence 112 having a polymer chain 114 carried on one strand. The aim of the assay is to determine whether any, and if so which, of the one or more fragments produced by the primer probes contains a sequence complementary to the probe sequence. In this example, the fragment 112 contains a region 116 whose base sequence is complementary to that of a known-sequence probe 118.

The fragments, such as fragment 112, are hybridized with the one or more labeled probes under standard hybridization conditions, binding probe 118 to the strand of fragment 116 which contains the polymer chain, thus forming modified, labeled probes which can be fractionated by electrophoresis, as above.

FIGS. 15A and 15B illustrate another method for modifying PCR-generated target fragments, such as double-stranded stranded fragment 130, composed of strands 132, 136. In the embodiment illustrated, strand 132 has been fluorescent-labeled with a reporter 134 at one fragment end during amplification. The fragment strand can be reporter labeled by a variety of methods, such as by nick translation or homopolymer tailing in the presence of labeled dNTP's, or by PCR amplification using a reporter-labeled primer.

The amplified fragments are mixed with a probe composition that includes a plurality of probes, such as probes 138, 140, 142, designed for sequence-specific binding to different-sequence regions of one strand of the target. Probe 138, which is representative, includes an oligonucleotide 144 having the desired region-specific base sequence, and a polymer chain 146 which imparts to each different-sequence probe, a distinctive ratio of charge/frictional drag.

In the method, the fragments are modified by hybridization, in single-stranded form, with the probes in the probe composition, forming fragments, such as fragment 150, with one or more double-stranded regions corresponding to probe binding. The modified fragments are reporter labeled in one strand and derivatized with one or more selected-length polymer chains in opposite strand probes. The modified fragments are then fractionated in double-stranded form by electrophoresis, to fractionate the fragments according to the number and size of polymer chains associated with each fragment.

Thus, for example, in the method illustrated, the fragment 132 binds probes 138, 142, and thus has been modified to carry a total of i+k polymer chain units. Since the fragments will migrate, on electrophoresis, with migration times which are dependent on the total number of polymer chain units attached to the fragments, the probe(s) associated with each fragment can be identified. This method can be used, for example to examine the distance between known sequences within genomic DNA, or for identifying linked sequences.

C. Probe Extension

A third general method for forming labeled probes, in accordance with the method of the invention, is illustrated in FIGS. 14A and 14B. In this method, a single-stranded target polynucleotide, such as shown at 120 in the figures, is reacted with a probe composition containing a plurality of probes, such as probe 122 which are designed for base specific binding to selected regions of the target. Probe 122, which is representative, is like probe 20 in FIG. 1A, and includes an oligonucleotide having a free 3'-end OH group and a selected-length polymer chain carried at its 5' end.

After binding the probes to the target, the probes are treated with DNA polymerase I, in the presence of at least one reporter-labeled dNTP, as shown. Dye-labeled dNTPs can be synthesized from commercial starting materials. For example, amino 7-dUTP (Clontech, Palo Alto, Calif.) can be reacted with fluorescein NHS ester (Molecular Probes, Eugene, Oreg.) under standard coupling conditions to form a fluorescein-labeled dUTP. The polymerase is effective, in the presence of all four nucleoside triphosphates, to extend the 3' end of target-bound probes, incorporating one or more labeled nucleotides, as indicated at 128, to form the desired modified, labeled probes having distinctive polymer chains associated with each different-sequence probe, characteristic of each probe sequence. Alternatively, in the above example, fluorescein may be coupled to the modified nucleotide, e.g., amino-7-dU, after incorporation into the probe. Each of the different-sequence modified, labeled probes has a distinct ratio of charge/translational frictional drag by virtue of its distinctive polymer chain.

After probe extension, the probes are released from the target and fractionated by electrophoresis, as above, to identify the migration positions of labeled probes corresponding to sequences contained in the target nucleotide.

D. Fragment Cleavage

Figure 17A:
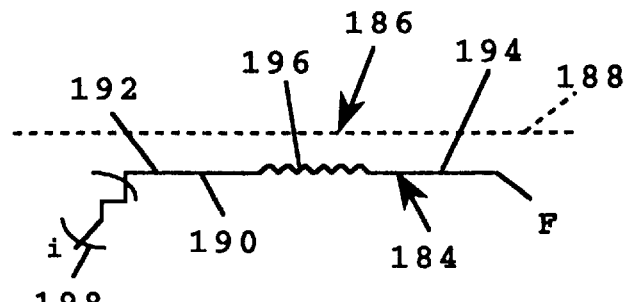
FIGS. 17A and 17B illustrate a method for identifying target sequences by selective probe cleavage, in accordance with a fourth general embodiment of the invention.
Figure 17B:
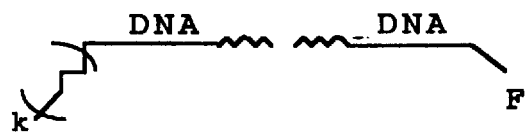

FIGS. 17A and 17B illustrate another embodiment of the method of the invention. In this method, the probe composition includes a plurality of sequence-specific probes, such as probe 184, designed for sequence specific binding to regions of a single-stranded target polynucleotide, such as region 186 in target polynucleotide 188. Probe 184, which is representative, includes a probe binding polymer 190 composed of a first single-stranded DNA segment 192, and a second segment 194 which includes single-stranded RNA region 196. A polymer chain 198 attached to the binding polymer's first segment imparts to the binding polymer, a distinctive charge/translational friction drag ratio, as discussed above. A reporter F is attached-to the second segment of the binding polymer. In particular, the polymer chain and reporter are on opposite sides of the RNA region, so that selective cleavage in this region will separate the probes first segment and attached polymer chain from the reporter.

In the method, the probe composition is reacted with the target polynucleotide under hybridization conditions, as above, to bind the probes in a sequence specific manner to complementary target regions. As seen in FIG. 17A, this produces a region of RNA/DNA duplex in each bound probe. The reaction mixture is now treated with a nuclease, such as RNase H, which is able to cut duplex RNA/DNA selectively (Duck), thus cutting each probe in its RNA binding region.

The hybridization reaction is now denatured, releasing, for each specifically bound probe, a modified labeled probe which lacks its polymer chain and thus now migrates as a free oligonucleotide by electrophoresis in a non-sieving medium. In an alternative embodiment (not shown), the polymer chain may be attached to the reporter side of the probe, i.e., to segment 192, so that RNAse treatment releases a portion of the binding polymer, modifying the combined charge/combined translational frictional drag of the labeled probe (which contains the polymer chain and reporter), thus shifting the electrophoretic mobility of the probe in a non-sieving medium, with respect to the uncleaved probe.

Figure 19A:
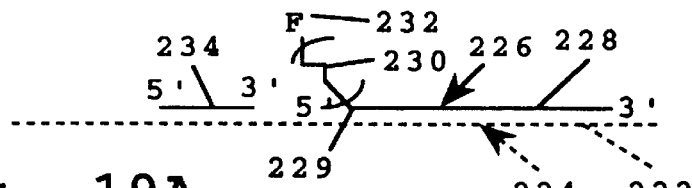
FIGS. 19A and 19B illustrate a method for modifying labeled probes by polymerase cleavage reaction, in accordance with the fourth general embodiment of the invention.

In another embodiment using the cleavage mode of generating labeled probe, probe modification is accomplished during extension of a primer annealed to the target polynucleotide upstream from (beyond the 5' end of) the annealed probe. This extension is produced by a DNA polymerase also incorporating a 5' to 3' exonuclease activity (Holland). The method is illustrated in FIG. 19A which shows a target polynucleotide 222 with a sequence region 224 of interest. The probes in this method are exemplified by probe 226 which contains a binding polymer 228 having a subunit 229 adjacent the polymer's 5' end. Attached to this subunit are a polymer chain 230 and a labeled probe 232 (which may be derivatized to the free end of the polymer chain). Also shown in the figure is a primer 234 which is designed for sequence specific binding to the target, upstream of the region 224.

Figure 19B:
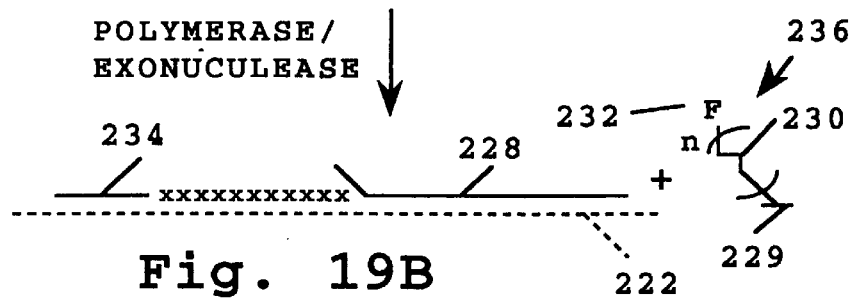

In practicing the method, the sequence-specific probes and a set of primers, such as primer 234, are reacted with the target polynucleotide under hybridization conditions, to bind associated probes and upstream primers to different-sequence regions of the target. The target and attached probes are now treated with the above polymerase in the presence of all four nucleoside triphosphates, resulting in extension of the primer in a 5' to 3' direction, as indicated by x's in FIG. 19B. As the polymerase reaches the 5' end of the adjacent probe, it cleaves off the 5' end subunits from the probe. As shown in FIG. 19B, cleavage of the subunit 229 from the probe releases a labeled probe 236 composed of base 229, reporter 232, and polymer chain 230 which imparts to the labeled probe, a distinct ratio of charge/translational frictional drag.

It will be recognized by one skilled in the art of molecular biology that many variants of the cleavage mode are practical; using exonuclease activities not linked to polymerase activities (e.g., the N-terminal selective cleavage fragment from E. coli polymerase I and the exonuclease of bacteriophage λ), using the 3'→5' proofreading exonuclease activities of certain DNA polymerases (in which case the polymer chain 198 and the reporter F preferably are attached to the 3' end of the probe, and this 3' end comprises one or more nucleotides mismatched to the template polynucleotide 188 of FIG. 17A), or using any of a wide range of sequence-specific endonucleases such as the restriction endonucleases. In all of these cases, the preferred embodiment locates the reporter and the polymer chain on the same side of the cleavage site(s), such that they remain covalently linked subsequent to cleavage. Additional polymer chains may or may not be added to the probe on the opposite side of the cleavage site(s) from the reporter in order to optimize the resolution of labeled probes from unlabeled probes.

E. Probe Capture

Figure 20A:
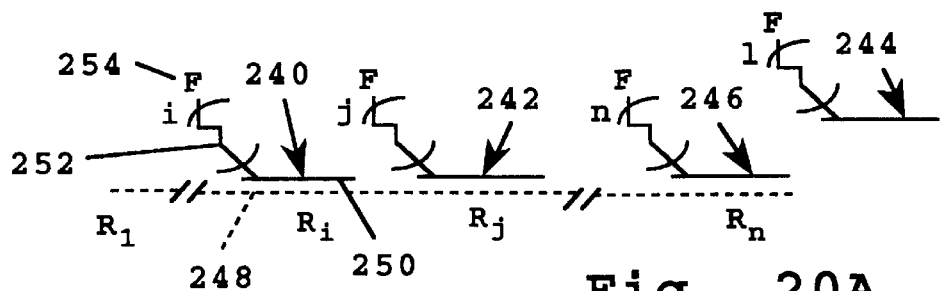
FIGS. 20A–20C illustrate steps in a probe capture method of identifying target equences, in accordance with a fifth general embodiment of the invention.
Figure 20B:
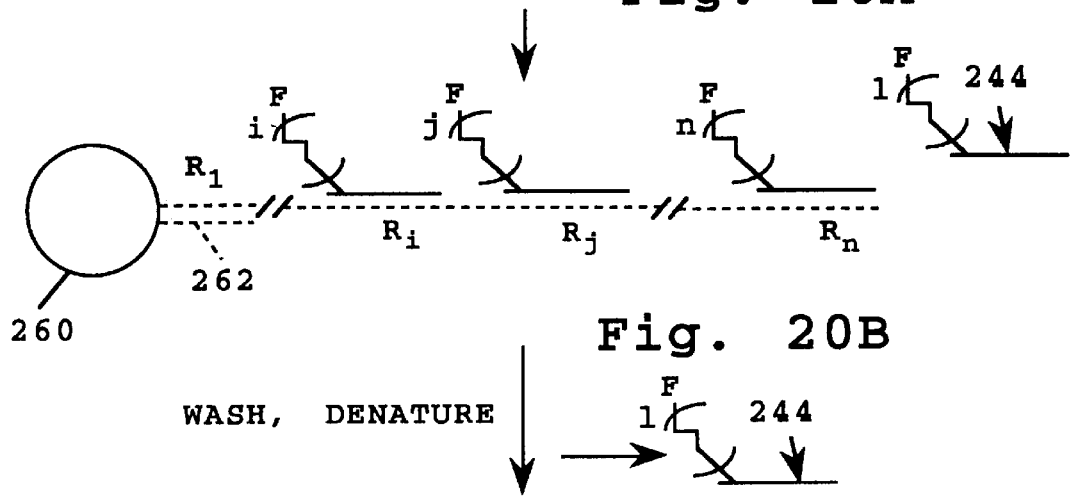
Figure 20C:
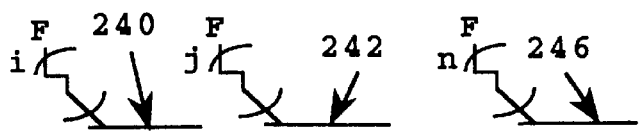

A fifth general embodiment, illustrated in FIGS. 20A–20C, involves probe capture and release from an immobilized target polynucleotide. FIG. 20A shows the addition of a plurality of probes, such as probes 240–246 to a target polynucleotide 248 containing differentsequence regions of interest, such as $R_i$, $R_j$, and $R_n$. Probe 240, which is representative, includes a binding polymer 250, a polymer chain 252 which imparts to that probe, a distinctive ratio of charge/translational frictional drag, and a reporter 254 attached to the binding polymer, in this case, to the polymer chain attached to the binding polymer. In the embodiment shown, each different-sequence probe has a different length polymer chain for achieving the distinctive charge/translational frictional drag ratio.

The probes are reacted with the target polynucleotide under hybridization conditions, as above. In the method illustrated in FIG. 20A, probes 240, 242, and 246 each hybridize with a complementary sequence in regions $R_i$, $R_j$, and $R_n$, respectively, of the target polynucleotide. It is assumed in this example that the target polynucleotide does not contain a region complementary to probe 244, leaving this probe unbound.

The target and hybridized probes are then treated to immobilize the target polynucleotide. This is done in the present example by adding a solid support 260 derivatized with an oligonucleotide probe 262 which is complementary to a region $R_1$ of the target polynucleotide, thus binding the target to the solid support, as indicated in FIG. 20B. The support and attached target and probes are now washed to remove non-specifically bound probes, such as probe 244.

In the final treating step, the washed solid support mixture is denatured to release bound probes, such as probes 240, 242, and 246, and these probes are then fractionated by electrophoresis in a non-sieving medium, to dentify target sequences, on the basis of distinctive electrophoretic positions of the fractionated, labeled robes.

From the foregoing, it will be appreciated how various objects and features of the invention are met. The method allows a plurality of target sequences to be assayed in a single-format assay, with rapid identification of sequences according to the migration distances (migration rates) of different-length polymer chains associated with sequence-specific labeled probes.

The polymer chains allow for separation of charged binding molecules, such as oligonucleotides, in a simple electrophoresis method which does not require a sieving matrix. In particular, this CE fractionation method allows for effective fractionation of a plurality of oligonucleotides, all of which have similar or identical sizes. One advantage of this feature is that the plural probes used in the method can all have similar or the same sizes, and thus can be hybridized with target sequences with about the same hybridization kinetics and thermodynamics ($T_m$).

The probes of the invention can be readily synthesized by conventional solid-phase methods. In one method, a polymer chain of a selected number of units can be formed directly on an oligonucleotide, by conventional solid-phase synthesis methods.

The following examples describe various aspects of making and using polymer-chain probes. The examples are intended to illustrate, but not limit the scope of the invention.

Materials

Hexaethylene glycol, 4,4',-dimethoxytrityl chloride, triethylamine, diisopropylethylamine, acetic acid, pyridine, methanesulfonyl chloride, sodium hydride, 2-cyanoethyl-N,N,N',N'-tetraisopropylphosphorodiamidite were obtained from Aldrich, Milwaukee, Wis. Diisopropylamine tetrazole salt, FAM-NHS/DMSO JOE-NHS/DMSO and TAMRA-NHS/DMSO were obtained from Applied Biosystems (ABI), Foster City, Calif. LAN (Linker Arm Nucleotide) 5'-dimethoxyl-trityl-5-(N-(7-trifluoroacetylaminoheptyl)-3-acrylamide)-2'-deoxyuridine-3'-phosphoramidite was obtained from Molecular Biosystems, Inc., San Diego, Calif.

Sephadex G-25M PD-10 columns were obtained from Pharmacia, Uppsala, Sweden. Derivatized oligonucleotides were LC purified using an ABI RP-300 (C8) column (4.6× 220 mm) using a flow rate of 1.5 ml/min and a gradient of 0.1M triethylammoniumacetate/water pH 7.0 and acetonitrile.

DNA synthesizer: 380B, ABI, Foster City, Calif.

EXAMPLE 1

Synthesis of $(HEO)_N$ Chains

The reactions described in this example are illustrated in FIG. 2 and are similar to those of Cload and Schepartz.
A. Dimethoxytrityl (DMT)-protected hexaethylene oxide (HEO)

27.0 gm (95.6 mmol) of HEO was dissolved in 100 ml pyridine. To this solution at room temperature was added a solution of 27.0 gm (79.7 mmol) of dimethoxytrityl chloride in 150 ml pyridine over 10 hr. The reaction was stirred at room temperature overnight (15 hr.) The solvent was removed in vacuo and the residue was brought up in 150 ml EtOAc and 100 ml $H_2O$, 2×100 ml brine and the organic layer was dried over $Na_2SO_4$. The solvent was removed to give a dark orange oil (38.36 gm). The crude material was purified by silica gel chromatography using 200 gm kiesel gel 60 and eluting with 2% methanol-methylene chloride (silica gel was basified with triethylamine). Appropriate fractions were combined to give 29.52 gm (50.49 mmol) of compound 1. Analysis of the DMT-protected HEO (compound 1 in FIG. 2) showed:

$^1$HNMR (300 MHz $CDCl_3$) δ7.5–6.8 (mult., 13H aromatic), 3.75 (S, 6H, $OCH_3$), 3.6 (20H, mult., $OCH_2$—$CH_2O$), 3.5 (2H, mult., $CH_2$—OH), 3.2 (2H, t, $CH_2ODMT$).
B. DMT-Protect HEO Phosphoramidite 1 gm (1.7 mmol) of DMT-protected HEO from Example 1A above and 0.029 g (0.17 mmol) of tetrazole diisopropyl ammonium salt were dissolved in 10 ml methylene chloride under inert atmosphere. To this was added 0.59 gm of 2-cyanoethyl tetraisopropyl phosphordiamidite, and the mixture was stirred overnight at room temperature. The reaction mixture was washed with a saturated solution of $NaHCO_3$, brine and dried over $Na_2SO_4$. The solvent was removed to give 1.58 gm crude oil, and the product was purified by flash chromatography through silica gel and eluted with 50% EtOAc-hexane (silica gel was basified with triethylamine). 0.8 gm (1.3 mmol) of purified phosphoramidite (compound 2 in FIG. 2) was recovered.
C. DMT-protected HEO methanesulfonate (mesylate)

In 100 ml methylene chloride was dissolved 10.4 gm (17.8 mmol) of DMT-protected HEO from Example 1A above. The solution was ice cooled and 4.59 gm (35.6 mmol) of diisopropylethylamine was added, followed by the addition of 2.06 g (26.7 mmol) methanesulfonyl chloride. The reaction mixture was stirred for 30 minutes and then washed with a saturated solution of $NaHCO_3$, brine and dried over $Na_2SO_4$. The solvent was removed in vacuo to give 11.93 gm of the mesylate (compound 3 in FIG. 2).
D. DMT-protected HEO dimer To a suspension of 0.62 gm (26.9 mmol) of sodium hydride in 150 ml freshly distilled tetrahydrofuran at 10° C. was added 10.14 gm (36.0 mmol) of hexaethylene glycol over 1 minute, and the mixture was stirred for at room temperature for 30 minutes. To this was added a solution of 11.93 gm (17.9 mmol) of HEO mesylate from Example 1C above in 50 ml tetrahydrofuran. The reaction mixture was warmed to 40°–50° C. for 3 hours, after which the solvent was removed in vacuo and the residue was brought up in 150 ml of methylene chloride. This was washed with 3×100 ml $H_2O$, brine and dried over $Na_2SO_4$. The solvent was removed in vacuo to give a crude oil (13.37 gm), which was purified by silica gel chromatography as in Example 1A above. 10.0 gm of the DMT-protected HEO dimer (11.8 mmol) was recovered. Analysis of the material (compound 4 in FIG. 2) showed:

$^1$HNMR (300 MHz $CDCl_3$) δ7.5–6.8 (mult., 13H aromatic), 3.75 (S, 6H, $OCH_3$), 3.6 (20H, mult., $OCH_2$—$CH_2O$), 3.5 (2H, mult., $CH_2$—OH), 3.2 (2H, t, $CH_2ODMT$).
E. Phosphoramidite of the DMT-protected HEO dimer (Compound 5 in FIG. 2).

1 gm (1.17 mmol) of DMT-protected HEO dimer from Example 1D and 20 mg (0.12 mmol) of tetrazole diisopropyl ammonium salt were dissolved in 10 ml methylene chloride under inert atmosphere. To this at room temperature was added 0.409 gm (1.35 mmol) of 2-cyanoethyl tetraisopropyl phosphordiamidite. After 15 hr., the reaction was washed with saturated $NaHCO_3$, brine and dried over $Na_2SO_4$. The solvent was removed in vacuo to give crude oil (1.44 gm), which was purified by flash chromatography as in Example 1B. 0.76 gm (0.73 mmol) of purified product was recovered. Analysis of the purified material (compound 5 in FIG. 2) showed:

$^{31}$P-NMR ($CD_3CN$, H decoupled): δ151 (s).

EXAMPLE 2

Synthesis of $(HEO)_N$ Chains linked by Bisurethane tolyl Groups

Figure 3:
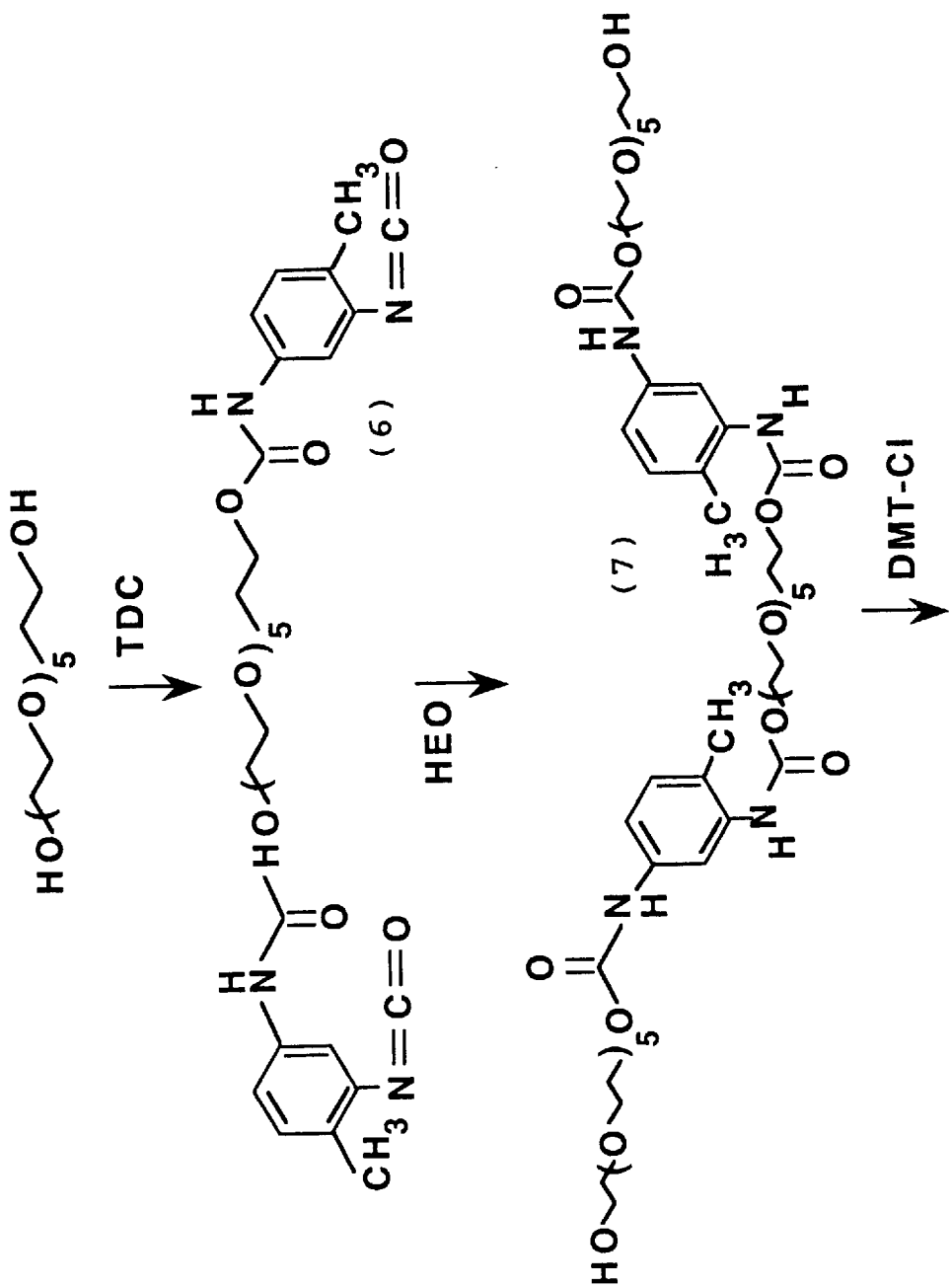
FIG. 3 illustrates methods of synthesis of polyethylene glycol polymer chains in which HEO units are linked by bisurethane tolyl linkages.

The reactions described in this Example are illustrated in FIG. 3.

Hexaethylene glycol (10.0 ml) was added dropwise to tolylene-2,4-diisocyanate (TDC) (17.0 ml) under argon at 30°–35° C. An ice bath was used to control the exothermic reaction. The reaction was allowed to stand at room temperature overnight; washed with hot hexane (10×) to remove excess diisocyanate; and concentrated under reduced pressure to yield the crude bisisocyanate product (compound 6, FIG. 3) as an amber oil (30 g).

A solution of the above crude bisisocyanate (2.3 g) and hexaethylene glycol (7.0 ml) in dichloromethane (25 ml) was stirred at room temperature for 1 hour and then dibutyltindilaurate (0.1 ml, Aldrich) was added and stirred at room temperature for 22 hours; diluted with dichloromethane and washed with water (4×20 ml); dried (MgSO4); and concentrated under reduced pressure to give the crude diol product (compound 7, FIG. 3) as an amber oil (4.6 g).

A solution of DMT chloride (1.2 g) in dichloromethane (20 ml) was added dropwise over 2 hours under argon at room temperature to a stirred solution of the above crude diol (4.4 g) and triethylamine (0.6 ml, Aldrich) in dichloromethane (25 ml). The reaction solution was stirred at room temperature for 2 hours and washed with water; dried (MgSO4); and concentrated under reduced pressure to give the crude DMT alcohol product as an amber oil (5.1 g). Column chromatography (triethylamine neutralized silica, 5% methanol/dichloromethane) of the crude DMT alcohol gave the purified DMT alcohol (compound 8, FIG. 3) as a viscous amber oil (0.72 g). Analysis of the compound showed: 1H NMR/CDCl$_3$: $\delta$6.7–7.5 (m, ArH, 19H), $\delta$4.3 (m, NC(O)OCH2, 8H), $\delta$3.77 (s, CH30, 6H), $\delta$3.55–3.75 (m, CH2OCH2, 62H), $\delta$3.2 (t, DMTOCH2, 2H), $\delta$2.15 (m, CH3Ar, 6H).

2 - C y a n o e t h y l - N , N , N - , N - tetraisopropylphosphorodiamidite (0.20 ml) was added under argon at room temperature to a stirred solution of the above purified DMT alcohol and tetrazole-diisopropylamine salt (12 mg) in dry dichloromethane (5 ml). After stirring at room temperature for 4 hours, NaHCO3 solution as added and stirred for 40 minutes. The dichloromethane layer was diluted with more dichloromethane and washed with brine; dried (MgSO4); and concentrated under reduced pressure to give the crude phosphoramidite product. (compound 9, FIG. 3) as an amber oil (0.88 g). $^{31}$P NMR (CDCl$_3$): 151 ppm.

EXAMPLE 3

Derivatization of Oligonucleotides with PEO Chains

The reactions described in Sections B and C are illustrated in FIGS. 4A and 4B, respectively.

A. Preparation of Oligonucleotide

A 48-base oligonucleotide having the sequence presented as 5'-SEQ ID NO:1 carboxyfluorescein-3' (composition 10 in FIG. 4A) was prepared using a 3'-linked carboxyfluorescein polystyrene support (Applied Biosystems, Inc.) or can be prepared using 3'-Amine-ON (oligonucleotide) CPG (Clontech, Palo Alto, Calif.) and FAM-NHS (ABI) according to published methods (Applied Biosystems, Caruthers, Connell) and standard phosphoramidite chemistry on an Applied Biosystems 380B DNA Synthesizer.

B. Oligonucleotide Derivatized with PEO Chain

The support-bound oligonucleotide from Example 3A above 0.1 $\mu$mol oligonucleotide was deprotected by reaction with trichloroacetic acid, washed, then reacted with one of the phosphoramidite-PEO polymers as in Example 1, using a standard DNA synthesis cycle. The embodiment shown in FIG. 4A is with polymer chain with 12 ethylene oxide subunits. The derivatized oligonucleotide (Compound 11 in FIG. 4A) was cleaved off the column with trityl on, and the collected product (compound 12 in FIG. 4A) was purified by liquid chromatography, using an ABI RP-300 (C-8) 4.6×220 mm column and a 0.1M triethylammonium acetate-water and acetonitrile solvent system. The derivatized oligonucleotide is shown as compound 12 in FIG. 4A.

C. Oligonucleotide derivatized with bisurethane tolyl-linked PEO Chain.

The support-bound oligonucleotide from Example 3A above (0.1 $\mu$mol oligonucleotide) (Compound 10, FIG. 4B) was reacted with a phosphoramidite-PEO bisurethane tolyl-linked polymer prepared as in Example 2 using a standard DNA synthesis cycle. (The tolyl-linked polymer indicated by subunit structure T-HEO-T-HEO in FIG. 4B corresponds to Compound ( in FIG. 3). The derivatized oligonucleotide (Compound 13 in FIG. 4B) was cleaved off the column and deprotected with trityl on, and purified by liquid chromatography, using an ABI RP-300 (C-8) 4.6×220 mm column and a 0.1M triethylammonium acetate-water and acetonitrile solvent system. The collected product was deprotected with acetic acid. The derivatized oligonucleotide is shown as compound 14 in FIG. 4B.

EXAMPLE 4

Successive PEO Additions to an Oligonucleotide

The reaction steps described in this Example are illustrated in FIG. 5.

A. FAM-labeled Oligonucleotide

A base oligonucleotide having the sequence presents as SEQ ID NO:3 was made as described in model 380B DNA synthesizer using standard phosphoramidite chemistry (composition 15 in FIG. 5). LAN is a base modified deoxyuridine phosphoramidite (Molecular Biosystems Inc.) with a TFA protected amine. The 26 mer was made from a 1 $\mu$m column using trityl on manual protocol after completion of synthesis. The column material was divided into 10 separate 0.1 $\mu$mol columns.

All of the subsequent oligos were cleaved off the support with NH$_4$OH and purified first by HPLC using an ABI RP-300 (C-8) column (4.6×220 mm) using a flow rate of 1.5 ml/min. and a solvent gradient of 0.1M triethylammonium acetate-water pH 7.0 and acetonitrile, then after the specific modifications described below, the trityl is removed and the product were isolated by HPLC using the conditions described above.

The cleaved oligonucleotides were labeled with FAM by adding a solution of the amine-labeled 26 mer with 15 $\mu$l of FAM•NHS in DMSO (ABI) and 40 $\mu$l of 1M NaHCO$_3$/Na$_2$CO$_3$ pH 9.0. After 2 hours the reaction mixtures were passed through a Pharmacia PD-10 Sephadex G25M column (Pharmacia) and the collected samples were then HPLC purified. After removal of the solvent the samples are detritylated with 80% acetic acid-water. The solvent was then removed in vacuo and the residue was brought up in 0.5 ml H$_2$O and is LC purified.

B. FAM Labeled PEO-Derivatized oligonucleotides

DMT-protected phosphoramidite HEO units from Example 1B were added to the 5' end of the oligo from Example 4A by standard phosphoramidite chemistry on solid support, yielding the composition 16 in FIG. 5. One to four units were added on in separate reactions. The resulting HEO modified oligos were cleaved from the solid support (Compound 17, FIG. 5) as above, and labeled with FAM and purified (Compound 18, FIG. 5), also as described above.

C. PEO-Derivatized Oligonucleotides

A 25 base oligonucleotide having the sequence presents as SEQ ID No:3 was made as described in Example 4A. DMT-protected phosphoramidite HEO units were added to the 5' end of this 25 mer and purified as described in Example 4B.

EXAMPLE 5

Conjugation of a Peptide to an Oligonucleotide

A 25 mer oligonucleotide was synthesized on CPG solid support with an ABI DNA synthesizer. To the 5' hydroxyl of the CPG supported oligonucleotide was added N-MMT-$C_6$ Amino Modifier using standard phosphoramidite chemistry. This is a monomethoxytrityl protected amino linked phosphoramidite which is commercially available from Clontech Laboratories, Palo Alto, Calif. The monomethoxytrityl group was removed using a standard trityl cleavage protocol on a DNA synthesizer and the DNA synthesis column was then placed on an ABI Peptide synthesizer capable of performing FMOC chemistry. Using standard FMOC peptide synthesis protocols, a four and an eight unit amino acid peptide was conjugated onto the 5'-terminal amine of the CPG supported oligonucleotide. After completion of the synthesis, the terminal amine of the peptide was acetylated using a standard peptide capping protocol.

The synthesis column was then placed onto an ABI DNA synthesizer and the peptide-oligonucleotide was cleaved off the support and p25 preview HPLC using the conditions as previously described to produce the peptide-oligonucleotides Ac (Phe-Ala)$_2$ or $_4$-NH(CH$_2$)$_6$-phosphate-5' SEQ ID NO: 3 GGC ACC ATT AAA GAA-AAT ATC ATC T-3'. Ligation of the peptide-oligonucleotide to a fluorescent-labeled oligonucleotide in the presence of an oligonucleotide target was performed as described in Example 7A. CE analysis is shown in FIG. 9.

EXAMPLE 6

Capillary Electrophoretic Separation of Probes

Capillary electrophoresis (CE) was carried out using a CE breadboard including a laser-based detector. The system includes a high-voltage power supply, a manual vacuum pump, and a PMT detector with a 530 nm RDF filter on the detected light. The laser was a 40 mW Ar ion laser. The capillary tube used in the system was a fused silica capillary tube 55 cm long with a 50 μm i.d. and 350 μm.

The grounded cathodic reservoir and the anodic reservoirs were filled with 75 mM tris-phosphate, pH 7.6, containing 8M urea.

A DNA mixture containing the four 26 mer oligonucleotides derivatized with 0, 1, 2, or 4 phosphate-linked HEO units, prepared as in Example 4, was diluted with 89 mM tris-borate buffer, pH 7.6, to a final DNA concentration of about $10^{-8}$M. About 2 nanoliters of the DNA solution was drawn into the cathodic end of the tube by electrokinetic injection.

The electrophoretic system was run at a voltage setting of about 15 kV (about 270 V/cm) throughout the run. Fluorescence detection was at 530 nm. The detector output signal was integrated and plotted on an HP Model 3396A integrator/plotter.

The electropherogram obtained is shown in FIG. 6. The numbers above the major peaks are electrophoresis times, in minutes. Total run time was about 22 minutes. The fastest-running peak, having a run time of 20.397 minutes, corresponds to the underivatized oligonucleotide. The oligonucleotides with 1, 2, and 4 HEO groups have migration peak times of 20.612, 20.994, and 21.559, respectively.

EXAMPLE 7

Template Derived Probes and Electrophoretic Separation

A. Ligation of Probe Elements

A first probe having the sequence

The oligonucleotide presented as SEQ ID NO:3 was derivatized with either a tetrapeptide (SEQ ID NO:4) or an octapeptide (SEQ ID NO:5) according to methods in Example 5. A second probe having the sequence presented as 5'-SEQ ID NO:6-JOE 3' was prepared by standard methods.

The probes were targeted against a 48-base oligonucleotide representing the F508 region of the cystic fibrosis gene. Probe hybridization to the target and ligation of the hybridized probes was performed substantially as follows:

Peptide-derivatized oligonucleotide (50 nM, 20 μl), and the fluorescence-labeled oligonucleotide (50 nM, 20 μl) were mixed with target oligonucleotide (50 nM, 20 μl); salmon sperm DNA (4 ug/10 μl, 20 μl); 10× reaction buffer (200 mM Tris.HCl pH 7.1; 1M KCl; 100 mM MgCl$_2$; 100 mM dithiothreitol; 10 mM nicotinamide-adeninedinucletide) (20 μl); ligase (30 units, 100 units/μl, Epicentre Technologies Ampligase, Madison, Wis.) and 100 μl of distilled water. The prepared sample was overlayed with 50 ul of oil and heated in a Perkin-Elmer Cetus DNA Thermal Cycler (Norwalk, Conn.) at 94° C. for 3 minutes and then at 62° C. for 60 minutes.

B. Capillary Electrophoretic Separation of Probes in a Non-Sieving Medium

A released ligated and non-ligated probe from above was ethanol precipitated and analyzed by CE electrophoresis in a non-sieving matrix. The capillary tube was a DB-5-coated capillary (J & W Scientific, Folsom, Calif.), 55 mm long, 40 mm to detector. The capillary was coated with a 0.5% surfactant solution prior to electrophoresis to render the capillary wall more hydrophilic. A variety of surfactants, such as BRIJ™ and TWEEN™ jeffamine class surfactants, are available for this purpose.

A 10 μl sample, heated to 95° C. for 2 minutes, was drawn into the tube. The buffer medium and electrophoresis medium was a 75 mM Tris-phosphate buffer, pH 8.0, 8M urea, 10% (v/v) MeOH. Electrophoretic run conditions were as described in Example 6. The electropherogram results are shown in FIG. 9, discussed above.

EXAMPLE 8

LCR Amplification and Separation of Ligated Probes

The following four probes were prepared: (1) SEQ ID NO:3 derivatized at its 5' end with either a 2 or 4 unit DEO (dodecyl ethylene oxide) polymer chain, according to synthetic methods described in Example 4, except in this case the units are 12-mers (2 or 4 12-mers) of ethylene oxide; (2) 5' P-SEQ ID NO:6-3'-JOE, prepared as in Example 7; (3) 5' ROX-SEQ ID NO:7-3'—OH, prepared according to published methods (Applied Biosystems); and (4) 5'-P-SEQ ID NO:8-3' TAMRA, prepared with 3'-amine-ON CPG, 5'-phosphate-ON and Tamra-NHS (ABI) using published methods (Applied Biosystems, Caruthers, Connell).

Probes 1 and 2 are designed to span a portion of one strand of the F508 region of the cystic fibrosis gene, as in Example 7. Probes 3 and 4 are designed to span the same portion of the F508 region of the opposite strand of the gene. Ligase chain reaction was performed according to published methods (Winn-Deen). Briefly, LCR assays were carried out in 20 mmol/L Tris.HCl buffer, pH 7.6, containing 100 mmol of K$^+$, 10 mmol of Mg$^{2+}$, 10 mmol of dithiothreitol, 1 mL of Triton X-100, and 1 mmol of AND$^+$ per liter. Each 100 µL of reaction mixture contained 1 pmol of each of the four oligonucleotides and 15 U of thermal-stable ligase (Epicentre Technologies, Madison, Wis.). To mimic the complexity of the human genome, we added 4 µg of herring sperm DNA to each reaction mixture. Reactions were carried out in 100-µL aliquots overlayed with 100 µL of mineral oil in Thin Walled Gene-Amp™ (Perkin-Elmer Cetus, Norwalk, Conn.) reaction tubes. All LCR reactions were run in a Perkin-Elmer Cetus model 9600 thermal cycler for 30 cycles of 94° C. (10S) and 60° C. (2 min). At the end of the cycling protocol, the reactions were cooled to 4° C.

The sample was ethanol precipitated and analyzed by CE electrophoresis in a non-sieving matrix. The capillary tube was a coated capillary, as in Example 7. A 10 µl sample, heated to 95° C. for 2 minutes, was drawn into the tube. The buffer medium and electrophoresis medium was a 75 mM Tris-phosphate buffer, pH 8.0, 8M urea, 10% (v/v) MeOH. Electrophoretic run conditions were as described in Example 7. The electropherogram results are shown in FIG. 11, discussed above.

Although the invention has been described with reference to various applications, methods, and compositions, it will be appreciated that various changes and modification may be made without departing from the invention.

It is claimed:

1. A method of detecting one or more different sequences in one or more target polynucleotide(s), comprising
adding to the target polynucleotide(s), a plurality of sequence-specific probes, each characterized by (a) a binding polymer having a probe-specific sequence of subunits designed for base-specific binding of the binding polymer to a target sequence, under selected binding conditions, and (b) attached to the binding polymer, a polymer chain having a ratio of charge/translational frictional drag which is different from that of the binding polymer,
reacting the probes with the target polynucleotide(s) under conditions favoring binding of the probes in a base-specific manner to the target polynucleotide(s),
treating the probes to selectively modify those probes which are bound to the target polynucleotide(s) in a sequence-specific manner, to form treated labeled probes characterized by (a) a distinctive ratio of charge/translational frictional drag, and (b) a detectable reporter label, and
fractionating the treated, labeled probe(s) by electrophoresis in a non-sieving medium.

2. The method of claim 1, wherein the probe binding polymers are oligonucleotides.

3. The method of claim 1, wherein the different-sequence binding polymers have substantially the same lengths, as evidenced by the ability of the binding polymers to hybridize to their associated target sequences with substantially the same hybridization reaction kinetics.

4. The method of claim 1, wherein said fractionating is carried out by capillary electrophoresis.

5. The method of claim 1, wherein (i) each sequences-specific probe includes first and second probe elements having first and second oligonucleotides effective to bind to adjacent regions of a target sequence, where one of the oligonucleotides is derivatized with said polymer chain, (ii) said reacting is effective to bind both oligonucleotides to its specific target sequence, (iii) said treating includes ligating the oligonucleotides bound to the target polynucleotide under conditions which are effective to ligate the end subunits of target-bound oligonucleotides when their end subunits are base-paired with adjacent target bases, to form the ligated probes, and releasing the ligated probe from the target polynucleotide, and (iv) the polymer chain attached to each different-sequence first oligonucleotide is effective to impart to the modified, labeled probe, a distinctive ratio of charge/transitional frictional drag.

6. The method of claim 5, wherein the second probe element is reporter labeled, and said ligating is carried out with ligase enzyme.

7. The method of claim 5, wherein said treating further includes subjecting the ligated probe to repeated cycles of probe binding and ligation, to amplify the concentration of ligated probe.

8. The method of claim 5, wherein said treating includes subjecting each ligated probe to repeated cycles of probe binding and ligation in the presence of a second pair of probe elements having oligonucleotides which, together, make up a sequence which is complementary to the selected ligated probe, to amplify the ligated probe in a exponential manner.

9. The method of claim 5, wherein said second probe element in each probe pair includes two alternative-sequence oligonucleotides which (i) are complementary to alternative sequences in the same portion of the associated target region and (ii) are derivatized with different detectable reporters, and said detecting includes determining the sequence of each of said regions according to (a) a signature electrophoretic migration rate of each probe, which identifies the target region associated with that probe, and (b) a signature reporter moiety, which identifies the ation state of that region.

10. The method of claim 1, wherein (i) each sequence-specific probe includes first and second primer elements having first and second sequence-specific oligonucleotides effective to hybridize with opposite end regions of complementary strands of a target polynucleotide segment, respectively, where the oligonucleotide in the first primer element is derivatized with such probe-specific selected-polymer chain, (ii) said reacting is effective to bind both primer oligonucleotides to opposite end regions on complementary strands of the target polynucleotide, (iii) said treating is effective to amplify the target segment by primer-initiated polymerase chain reaction, and (iv) the polymer chain attached to each different-sequence first oligonucleotide is effective to impart to the amplified target sequences, a distinctive ratio of charge/translational frictional drag.

11. The method of claim 10, wherein the oligonucleotide in the second primer element is reporter labeled, and the labeled probes are double stranded polynucleotide fragments.

12. The method of claim 10, wherein said treating further includes hybridizing to the amplified target sequences, with such in single-stranded form, single-stranded, reporter-labeled oligonucleotides whose sequences are complementary to regions of the amplified target sequences, to form labeled probes.

13. The method of claim 2, wherein each sequence-specific probe includes a binding polymer and an attached reporter label, the polymer chain associated with eachdifferent-sequence probe imparts to that probe, a distinctive ratio of charge/translational frictional drag, and said treating includes reacting the hybridized probes and target with DNA polymerase in the presence of a reporter-labeled nucleoside triphosphate molecule, to form said labeled probes.

14. The method of claim 2, wherein each sequence-specific probe includes a binding polymer composed of first and second single-stranded DNA segments which flank a single-stranded RNA segment, where the polymer chain is attached to said first DNA segment, and a reporter is attached to said second DNA segment, and said treating includes reacting hybridized probe with an RNase enzyme specific for RNA/DNA substrate, to form modified, labeled probes lacking the polymer chains.

15. The method of claim 2, wherein each sequence-specific probe includes a binding polymer composed of a first single-stranded DNA segment, and a second segment which includes single-stranded RNA, the polymer chain and reporter label are attached to said first segment, and said treating includes reacting hybridized probe with an RNase enzyme specific for RNA/DNA substrate, to form modified, labeled probes lacking said second binding polymer segments.

16. The method of claim 2, wherein each sequence-specific probe includes (i) an oligonucleotide binding polymer having a 5' end, where said polymer chain and a reporter label are attached to an oligonucleotide subunit adjacent said 5' end, and (ii) a primer designed for sequence-specific binding to the target upstream of said binding polymer, and said treating includes exposing immobilized probe to a DNA polymerase having a 5' to 3' exonuclease activity under conditions effective to extend said primer toward said binding polymer, said exposing being effective to enzymatically cleave said adjacent subunit from the binding polymer, forming a labeled probe whose polymer chain imparts to the probe, a distinctive charge/translational frictional drag.

17. The method of claim 1, wherein each sequence-specific probe includes a binding polymer and an attached reporter label, the polymer chain associated with each different-sequence probe imparts to that probe, a distinctive ratio of charge/translational frictional drag, and said treating includes immobilizing said target polynucleotide, washing the immobilized target polynucleotide to remove probes not bound to the target polynucleotide in a sequence-specific manner, and denaturing the target polynucleotide to release probes bound in a sequence-specific manner.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: 48-BASE OLIGONUCLEOTIDE, PAGE 46

( x i ) SEQUENCE DESCRIPTION: SEQ ID NO:1:

GCACCATTAA AGAAAATATC ATCTTTGGTG TTTCCTATGA TGAATATA    48

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: 26-BASE OLIGONUCLEOTIDE, PAGE 47

( x i ) SEQUENCE DESCRIPTION: SEQ ID NO:2:

TTGGTGTTTC CTATGATGAA TATA    24

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: 25-BASE OLIGONUCLEOTIDE, PAGE 48

( x i ) SEQUENCE DESCRIPTION: SEQ ID NO:3:

GGCACCATTA AAGAAAATAT CATCT 25

( 2 ) INFORMATION FOR SEQ ID NO:4:

( i ) SEQUENCE CHARACTERISTICS:
  ( A ) LENGTH: 4 amino acids
  ( B ) TYPE: amino acid
  ( D ) TOPOLOGY: linear ( i i ) MOLECULE TYPE: peptide ( i i i ) HYPOTHETICAL: NO ( v i ) ORIGINAL SOURCE:
  ( C ) INDIVIDUAL ISOLATE: TETRAPEPTIDE, PAGE 28

( x i ) SEQUENCE DESCRIPTION: SEQ ID NO:4:

Phe Ala Phe Ala
1

( 2 ) INFORMATION FOR SEQ ID NO:5:

( i ) SEQUENCE CHARACTERISTICS:
  ( A ) LENGTH: 8 amino acids
  ( B ) TYPE: amino acid
  ( D ) TOPOLOGY: linear ( i i ) MOLECULE TYPE: peptide ( i i i ) HYPOTHETICAL: NO ( v i ) ORIGINAL SOURCE:
  ( C ) INDIVIDUAL ISOLATE: OCTAPEPTIDE, PAGE 51

( x i ) SEQUENCE DESCRIPTION: SEQ ID NO:5:

Phe Ala Phe Ala Phe Ala Phe Ala
1               5

( 2 ) INFORMATION FOR SEQ ID NO:6:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( v i ) ORIGINAL SOURCE:
  ( C ) INDIVIDUAL ISOLATE: 25-BASE OLIGONUCLEOTIDE, PAGE 52

( x i ) SEQUENCE DESCRIPTION: SEQ ID NO:6:

TTGGTGTTTC CTATGATGAA TATAG 25

( 2 ) INFORMATION FOR SEQ ID NO:7:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( v i ) ORIGINAL SOURCE:
  ( C ) INDIVIDUAL ISOLATE: 26-BASE OLIGONUCLEOTIDE, PAGE 52

(x i) SEQUENCE DESCRIPTION: SEQ ID NO:7:

CTATATTCAT CATAGGAAAC ACCAAA                                              2 6

(2) INFORMATION FOR SEQ ID NO:8:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (i i) MOLECULE TYPE: DNA (genomic)

(i i i) HYPOTHETICAL: NO (v i) ORIGINAL SOURCE:
      (C) INDIVIDUAL ISOLATE: 24-BASE OLIGONUCLEOTIDE, PAGE 52

(x i) SEQUENCE DESCRIPTION: SEQ ID NO:8:

GATGATATTT TCTTTAATGG TGCC                                                2 4